United States Patent [19]
Sebti et al.

[11] Patent Number: 6,011,175
[45] Date of Patent: *Jan. 4, 2000

[54] INHIBITION OF FARNESYLTRANSFERASE

[75] Inventors: Said Sebti; Andrew Hamilton, both of Pittsburgh, Pa.

[73] Assignee: University of Pittsburgh, Pittsburgh, Pa.

[*] Notice: This patent is subject to a terminal disclaimer.

[21] Appl. No.: 08/582,076

[22] Filed: Jan. 2, 1996

Related U.S. Application Data

[63] Continuation-in-part of application No. 08/371,682, Jan. 12, 1995, Pat. No. 5,705,686, which is a continuation-in-part of application No. 08/062,287, May 18, 1993, Pat. No. 5,602,098.

[51] Int. Cl.$^7$ .................................................. C07C 321/02
[52] U.S. Cl. ............................................. 562/557; 514/19
[58] Field of Search .............................. 514/18; 562/557, 562/559, 445; 530/331, 332, 323

[56] References Cited

U.S. PATENT DOCUMENTS

| | | | |
|---|---|---|---|
| 5,043,268 | 8/1991 | Stock ........................................ | 435/15 |
| 5,141,851 | 8/1992 | Brown et al. ............................. | 435/15 |
| 5,238,922 | 8/1993 | Graham et al. ........................... | 514/18 |
| 5,631,280 | 5/1997 | Ciccarone ................................. | 514/416 |

FOREIGN PATENT DOCUMENTS

| | | | |
|---|---|---|---|
| 2072033 | 6/1992 | Canada . | |
| 0203587 | 12/1986 | European Pat. Off. . | |
| 0456180 | 11/1991 | European Pat. Off. . | |
| 0461869 | 12/1991 | European Pat. Off. . | |
| 0512865 | 11/1992 | European Pat. Off. . | |
| 0520823 | 12/1992 | European Pat. Off. . | |
| 0523873 | 1/1993 | European Pat. Off. . | |
| 0528486 | 2/1993 | European Pat. Off. ......... | C07K 5/10 |
| 0534546 | 3/1993 | European Pat. Off. ......... | C07F 9/38 |
| 0535730 | 4/1993 | European Pat. Off. ......... | C07K 5/08 |
| WO91116340 | 10/1991 | WIPO . | |
| WO9218465 | 10/1992 | WIPO . | |
| WO94766 | 5/1994 | WIPO . | |

OTHER PUBLICATIONS

Sako, Chem Pharm Bull 40, 49, 1992.
Harrington, Bioorg. Med. Chem. Lett. 4, 2775, 1994.
Uete J. Chem. Clin. Biochem. 19, 145, 1981.
Lalu Biochim Biophys Acta 873, 190 1986.
Hancock et al, "A polybasic Domain or Palmitoylation is Required in Addition to the CAAX Motif to Localize p21$^{ras}$ to the Plasma Membrane". Cell, vol. 63, Oct. 5, 1990, pp. 133–139.
Reiss et al, "Inhibiting of Purified p21$^{ras}$ Farnesyl:Protein Transferase by Cys–AAX Tetrapeptides", Cell, vol. 62, Jul. 13, 1990, pp. 81–88.
Willumsen et al, "The p21 ras C–terminus is required for transformation and membrane association," Nature, vol. 310, Aug. 16, 1984, pp. 583–586.

Gibbs, J.B., Ras C–Terminal Processing Enzymes—New Drug Targets, Cell, 65:1–4 (1991).
Gibbs et al., Farnesyltransferase Inhibitors: Ras Research Yields a Potential Cancer Terapeutic, Cell, 77:175–178 (1994).
Brown et al., Tetrapeptide inhibitors of protein farnesyltransferase: Amino–terminal substitution in phenylalanine––containing tetrapeptides restores farnesylation, Proc. Natl. Acad. Sci. U.S.A., 89:8313–8316 (1992).
Kohl et al., Selective Inhibition of ras–Dependent Transformation by a Farnesylatransferase Inhibitor, Science, 260:1934–1937 (1993).
Graham et al., Pseudopeptide Inhibitors of Ras Farnesyl––Protein Transferase, J. Med. Chem., 37:725–732 (1994).
Garcia et al., Peptidomimetic Inhibitors of Ras Farnesylation and Function in Whole Cells, J. Biol. Chem., 268:18415–18418 (1993).
Nigam et al., Potent Inhibition of Human Tumor p21$^{ras}$ Farnesyltransferase by $A_1A_2$—lacking p21$^{ras}$ $CA_1A_2X$ Peptidomimetics, J. Biol. Chem., 268:20695–20698 (1993).
Qian et al., Design and Structural Requirements of Potent Peptidomimetic Inhibitors of p21$^{ras}$ Farnesyltransferase, J. Biol. Chem., 269:12410–12413 (1994).
Qian et al., Peptidomimetic Inhibitors of P21RAS Farnesyltransferase: Hydrophobic Functionalization Leads to Distruption of P21RAS Membrane Association in Whole Cells, Bioorg. Med. Chem. Lett., 4:2579–2584 (1994).
Goldstein et al., Benzodiazepine Peptidomimetics: Potent Inhibitors of Ras Farnesylation in Animal Cells, Science, 260:1937–1942 (1993).

(List continued on next page.)

*Primary Examiner*—Cecilia J. Tsang
*Assistant Examiner*—David Lukton
*Attorney, Agent, or Firm*—Cushman Darby & Cushman IP Group of Pillsbury Madison & Sutro

[57] ABSTRACT

A compound of the formula $$C^oB$$

wherein
$C^o$ stands for

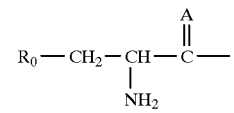

A representing O or 2H, and
$R_0$ representing SH, $NH_2$, or $C_xH_y$—$SO_2$—NH—, wherein $C_xH_y$ is a straight chain saturated or unsaturated hydrocarbon, with x being between 1 and 20 and y between 3 and 41, inclusive; and
B stands for —NHR, where R is an aryl group.
The compounds are useful for inhibiting p21ras farnesyltransferase.

21 Claims, 5 Drawing Sheets

OTHER PUBLICATIONS

Reiss et al., Inhibition of Purified p21$^{ras}$ Farnesyl:Protein Transferase by Cys–AAX Tetrapeptides, Cell, 62:81–88 (1990).

Vogt et al., A Non–peptide Mimetic of Ras–CAAX:Selective Inhibition of Farnesyltransferase and Ras Processing, (1995) J. Biol. Chem. 270:660–664.

Kohl et al., Protein farnesyltransferase inhibitors block the growth of ras–dependent tumors in nude mice, (1994) Proc. Natl. Acad. Sci. USA 91:9141–9145.

Cox et al., The CAAX Peptidomimetic Compound B581 Specifically Blocks Farnesylated, but Not Geranylgeranylated or Myristylated, Oncogenic Ras Signaling and Transformation, (1994) J. Biol. Chem. 269:19203–19206.

Lerner et al., Ras CAAX Peptidomimetic FTI–277 Selectively Blocks Oncogenic Ras Signaling by Inducing Cytoplasmic Accumlation of Inactive Ras–Raf Complexes (1995) J. Biol. Chem. 270:26802–26806.

Sun et al., Ras CAAX Peptidomimetic FTI 276 Selectively Blocks Tumor Growth in Nude Mice of a Human Lung Carcinoma with K–RAS Mutation and p53 Deletion, (1995) Cancer Research 55, 4243–4247.

FIG. 1

4 : R¹=COOH    R²=H
5 : R¹=H       R²=COOH
8 : R¹=CH₃     R²=H

Ras

FIG. 5A

Rap1A

FIG. 5B

INHIBITION OF FARNESYLTRANSFERASE

The present application is a continuation-in-part of U.S. application Ser. No. 08/371,682, filed Jan. 12, 1995, now U.S. Pat. No. 5,705,686 which is a continuation-in-part of allowed U.S. application Ser. No. 08/062,287, filed May 18, 1993, now U.S. Pat. No. 5,602,098 the contents of both are incorporated herein by reference.

This invention was supported by grants from the National Cancer Institute (NIH). The government has certain rights in the invention.

BACKGROUND OF THE INVENTION

1. Field of the Invention

The present invention relates to novel non-peptide mimetics of CAAX (C=Cys, A=Leu, Ile or Val, X=Met or Ser) which are useful as inhibitors of Ras farnesyltransferase (FTase).

Cysteine farnesylation of the carboxyl terminal tetrapeptides CAAX of the oncogene product Ras is required for its malignant transformation activity. As a consequence, farnesyltransferase (FTase), the enzyme responsible for the essential lipid modification, has become one of the most sought after targets for anticancer drug development. Previously, proposed peptide mimics have shown potent inhibition of FTase in vitro but have certain undesirable peptide features that hamper their use in vivo. The invention is concerned with non-peptide mimetics of CAAX which are free from peptide amide groups and other peptidic features which are effective and selective for FTase inhibition both in vitro and in vivo.

2. Background Information

Ras is a small guanine nucleotide binding GTPase that transduces biological information from the cell surface to the nucleus (1). Its ability to transfer growth signals from receptor tyrosine kinases to a mitogen activated protein (MAP) kinase cascade puts it in the heart of signaling pathways that cause proliferation in normal cells and uncontrolled growth in cancer cells (2). Indeed, mutations that lock ras in its active, GTP-bound state lead to malignant transformation and are among the most frequently identified mutations in human cancers (1). For example, 50% of colorectal and 95% of pancreatic human cancers have activated ras oncogenes.

Over the last decade, several strategies have been investigated, with only moderate success, to disrupt Ras function and hence, to inhibit the growth of tumors with activated ras oncogenes. The search has recently intensified with the discovery that Ras requires lipid modification with a farnesyl group for localization to the plasma membrane where it plays a pivotal role in growth signaling (3–9). Because farnesylation is required and sufficient for ras membrane association and transformation (10), the enzyme that catalyzes this lipid modification, farnesyltransferase (FTase), has become a major target for the design of novel anticancer agents (11, 12).

FTase is a α and β heterodimer that transfers farnesyl from farnesylpyrophosphate, a cholesterol biosynthesis intermediate, to the cysteine of proteins containing the carboxyl terminal sequence CAAX (where C is cysteine, A is an aliphatic amino acid and X is any amino acid except Leu or Ile) (13, 14). A closely related prenyltransferase, geranylgeranyltransferase I (GGTase I) catalyzes cysteine geranylgeranylation of proteins ending in CAAX where X-Leu or Ile (15, 16). In contrast to FTase and GGTase I, a third prenyltransferase, GGTase II, does not recognize CAAX sequences but rather geranylgeranylates proteins ending in CC or CXC sequences (15, 16). Prenylation of CAAX sequences by FTase and GGTase I is followed by proteolysis of the tripeptide AAX and carboxymethylation of the resulting prenylated cysteine, whereas GGTase II-catalyzed reactions are not followed by further posttranslational modifications. Since the number of geranylgeranylated proteins in the cell far exceeds that of farnesylated proteins (15, 16), it is desirable that potential anticancer agents which act by targeting farnysylation be highly selective for FTase over GGTase I to minimize side effects.

Developing Ras CAAX tetrapeptide mimics as anticancer drugs has been prompted by the observation that FTase recognizes and farnesylates CAAX peptides which were also found to be potent competitive inhibitors of the enzyme ($IC_{50}s$=50–200 nM) (13, 17–22). However, because of their peptidic nature, CAAX peptides do not inhibit Ras processing in whole cells. To enhance their poor cellular uptake and decrease their sensitivity to cellular proteases, it has been proposed to make CAAX pseudopeptides (23–25). Reduction of the amino terminal and central amide bonds of CAAX, and neutralization of the free carboxylate resulted in greater activity in whole cells (23–25)

Although the FTase inhibitors discussed above are potent inhibitors in vitro, they still retain several peptidic features which leave the proposed inhibitors vulnerable to proteolytic degradation in cells. With this in mind, it has been proposed in U.S. Pat. No. 5,602,098 to modify prior CAAX tetrapeptide mimics by, for example, replacing the peptide portion VI in CVIM (SEQ ID NO.1), the carboxyl terminal of $K_B$-Ras, by a hydrophobic spacer such as 4-aminobenzoic acid (4-ABA) to link Cys to Met (i.e., Cys-4ABA-Met) (26–28). As an alternative, James et al (29) used a benzodiazepine group between cysteine and methionine. The latter suggested that the best disruption of FTase activity could be achieved when the inhibitors take up a β turn conformation that brings in close proximity the cysteine thiol and the methionine carboxylate to form a bidentate complex with a putative $Zn^{++}$ ion in the enzyme active site (29). However, conformational analysis of the inhibitor Cys-4ABA-Met described in U.S. Pat. No. 5,602,098 has shown that it could not take up a β-turn, arguing against this structural feature as a target for future FTase inhibitor design (27).

The compounds of U.S. Pat. No. 5,602,098 represent a significant improvement over prior FTase inhibitors. However, it is believed that even better results could be obtained if the amide bond or bonds or other peptidic features could be eliminated or at least reduced even further.

SUMMARY OF THE INVENTION

The principal object of the invention is to provide a group of non-peptide CAAX mimetics which contain no amide or hydrolyzable bonds. Basically these compounds comprise free cysteine thiol and/or terminal amino groups at one end and include a carboxylic acid or carboxylate group at the other end, the carboxylic acid or carboxylate group being separated from the cysteine thiol and/or terminal amino group by a hydrophobic spacer moiety which is free from any linking amido group as in prior CAAX mimetics. The present compounds are not subject to proteolytic degradation inside cells while retaining the structural features required for FTase inhibition. The compounds selectively inhibit FTase both in vitro and in vivo and offer a number of other advantages over prior CAAX peptide mimetics.

The compounds of the invention may be illustrated by the formula:

$C^0B$ where $C^0$ is

A represents O or 2H, and $R_0$ represents SH, $NH_2$, or $C_xH_y$—$SO_2$—NH—, wherein $C_xH_y$ is a straight chain saturated or unsaturated hydrocarbon, with x being between 1 and 20 and y between 3 and 41, inclusive; and B stands for —NHR, where R is an aryl group.

In a preferred embodiment of the invention, R is a biphenyl substituted with one or more —COOH groups and/or lower alkyl, e.g., methyl, as represented by the formula:

where $R_1$ and $R_3$ represent H or COOH;

$R_2$ represents H, COOH, $CH_3$, or $COOCH_3$;

$R_4$ represents H or $OCH_3$; and

A represents 2H or O.

This formula represents a series of 4-amino-3'-carboxybiphenyl derivatives which mimic the Val-Ile-Met tripeptide but have restricted conformational flexibility. Reduction of the cysteine amide bond (where A is H,H) provides a completely non-peptidic Ras CAAX mimetic.

Although the structures of these designed non-peptide CAAX mimetics are significantly different from that of the tetrapeptide Cys-Val-Ile-Met, the functional groups of free amine, thiol and carboxylic acids are retained. Because it appeared that an extended rather than a turn conformation of tetrapeptide 1 might be responsible for its inhibitory activity (15), an energy minimized conformation of compound 4 was calculated by using the AMBER force field within the MacroModel program in the absence of solvent and compared with the extended conformation of tetrapeptide 1. Molecular modeling (FIG. 2) shows that the designed non-peptide mimetic 4 has the functional groups arranged very similarly to the tetrapeptide 1 (SH to COOH distance about 10.5 Å). Furthermore, the hydrophobic biphenyl residue in 4 mimics the side chains of tripeptide Val-Ile-Met in 1 which provide a large hydrophobic area.

Preferably, R is a biphenyl group with a —COOH substitution in the 3'- or 4'-position, most preferably the 3'-position, with respect to the NH-aryl group. The —COOH substituent may appear as such or in pharmaceutically acceptable salt or ester form, e.g., as the alkali metal salt or methyl ester.

The features of the invention are illustrated herein by reference to the CAAX tetrapeptide known as CVIM (SEQ ID NO.1) (see EP 0461869 and U.S. Pat. No. 5,141,851) and C-4ABA-M which is disclosed in U.S. Pat. No. 5,602,098. These compounds are, respectively, Cys-Val-Ile-Met and Cys-4 aminobenzoic acid-Met where Cys is the cysteine radical and Met is the methionine radical.

Figure 1:
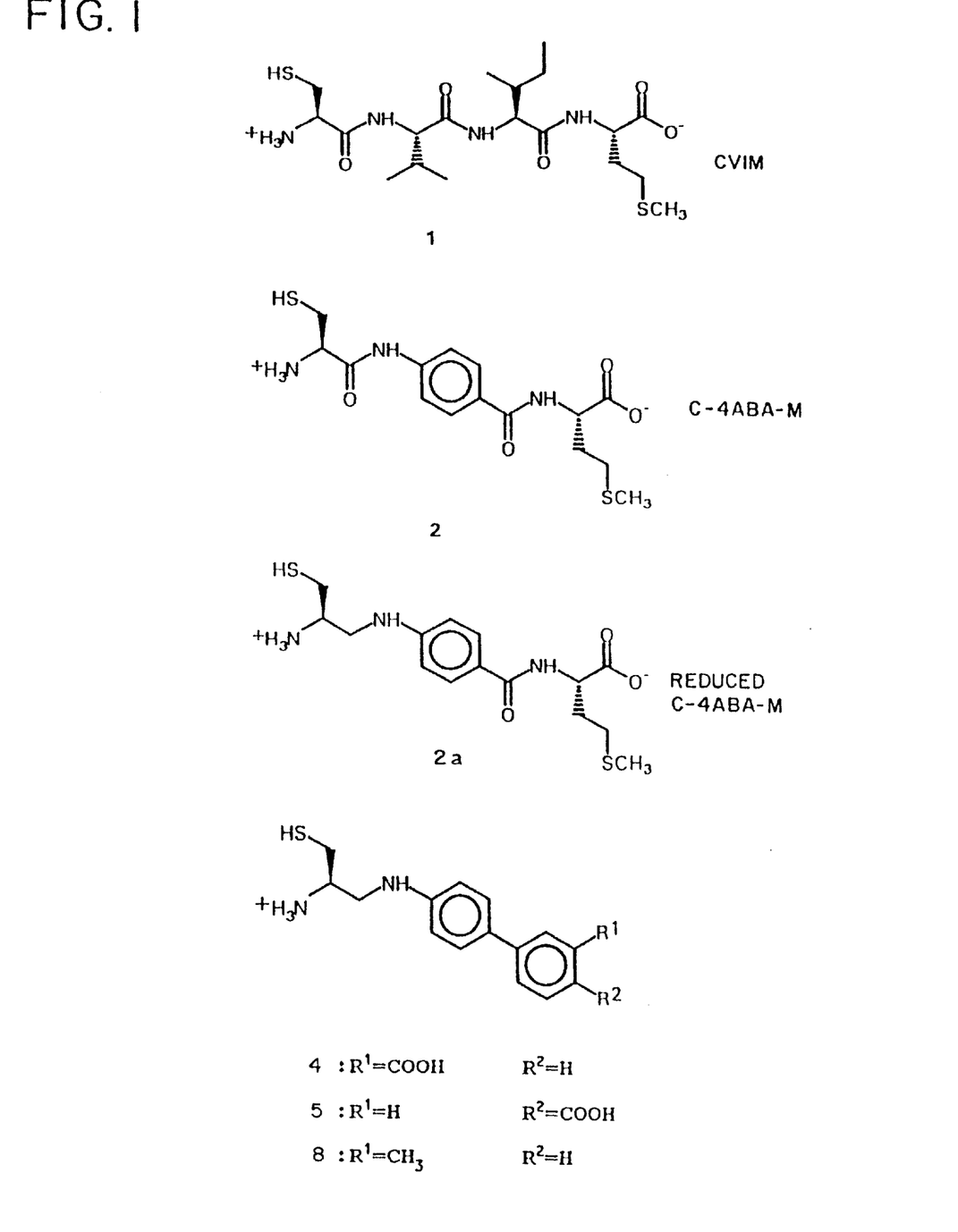
FIG. 1 illustrates the structures of previously disclosed peptidomimetics together with the compounds of the invention (4, 5 and 8)

A preferred non-peptide CAAX mimetic of the invention is reduced cys-4-amino-3'-biphenylcarboxylate identified as 4 (FIG. 1). This derivative contains no amide bonds and thus is a true non-peptide mimic of the CAAX tetrapeptide.

Figure 2:
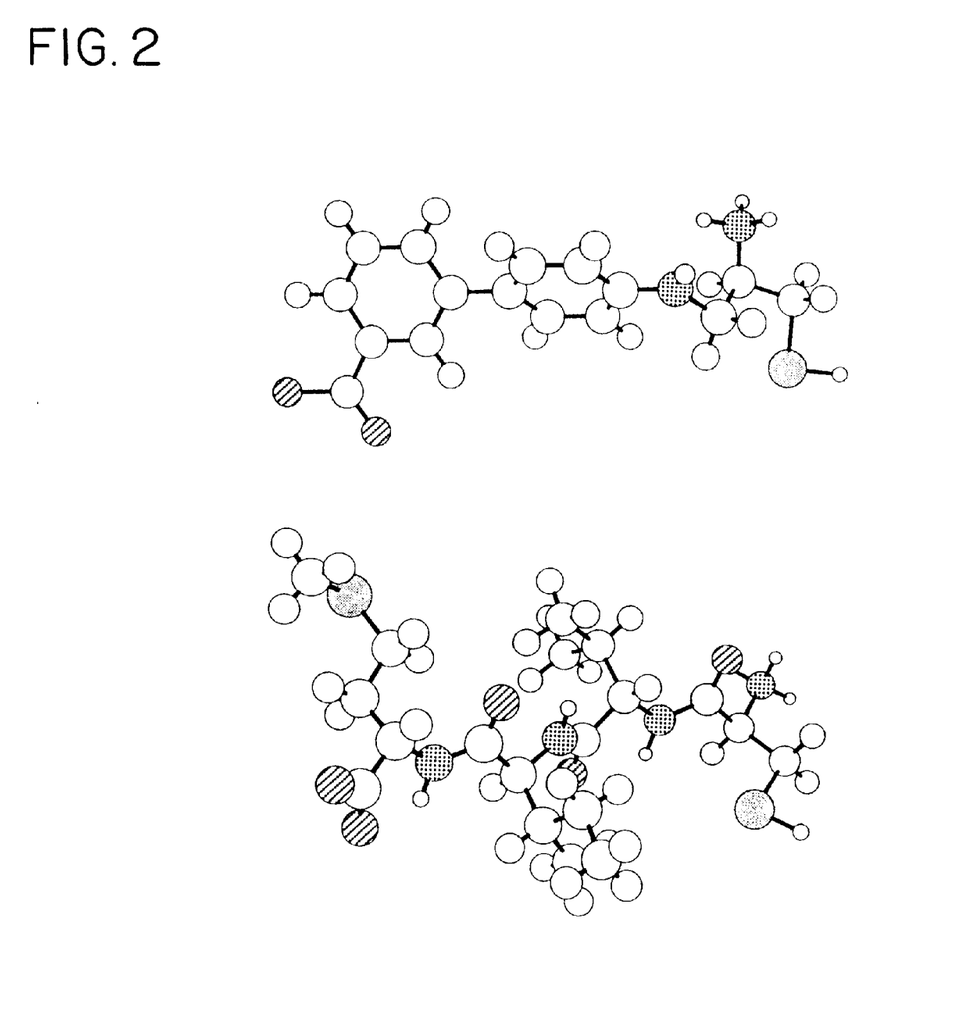
FIG. 2 illustrates the energy-minimized structural conformations for CVIM (SEQ ID NO.1) and compound 4 of the invention.

Although compound 4 and compounds 1, 2 and 2a (FIG. 1) are structurally quite different, they share several features that are important to FTase recognition. Most notably, they all have free cysteine thiol and terminal amino groups at the one end and carboxylate group on the other, these groups being separated by a hydrophobic moiety. Furthermore, molecular modeling studies indicate energy-minimized structures that show similar distances between the cysteine thiol and the free carboxylate in both compound 4 and CVIM (SEQ ID NO.1) in the extended conformation (FIG. 2).

Compounds 5 and 8 are also representative of the invention. While these compounds are somewhat less active than compound 4, their overall properties indicate effectiveness as FTase inhibitors.

The compounds of the invention may be used in the carboxylic acid form or as pharmaceutically acceptable salts or esters thereof. Lower alkyl esters are preferred although other ester forms, e.g., phenyl esters, may also be used.

The compounds of the invention may be used in the same manner as prior CAAX tetrapeptide inhibitors to inhibit p21ras farnesyltransferase in any host containing the same. This includes both in vitro and in vivo use. Because the compounds inhibit farnesyltransferase, notably human tumor p21ras farnesyltransferase, and consequently inhibit the farnesylation of the oncogene protein Ras, they may be used in the treatment of cancer or cancer cells. It is noted that many human cancers have activated ras and, as typical of such cancers, there may be mentioned colorectal carcinoma, myeloid leukemias, exocrine pancreatic carcinoma and the like.

The compounds of the invention may be used in pharmaceutical compositions of conventional form suitable for oral, subcutaneous, intravenous, intraperitoneal or intramuscular administration to a mammal or host. This includes, for example, tablets or capsules, sterile solutions or suspensions comprising one or more compounds of the invention with a pharmaceutically acceptable carrier and with or without other additives. Typical carriers for tablet or capsule use include, for example, lactose or corn starch. For oral compositions, aqueous suspensions may be used with conventional suspending agents, flavoring agents and the like.

The amount of inhibitor administered to obtain the desired inhibitory effect will vary but can be readily determined. For human use, daily dosages are dependent on the circumstances, e.g., age and weight. However, daily dosages of from 0.05 to 20 mg per kg body weight may be mentioned for purposes of illustration.

DESCRIPTION OF PREFERRED EMBODIMENTS

For ease of reference, the following abbreviations may be used in the present specification:
FTase: farnesyltransferase;
GGTase: geranylgeranyltransferase;
SDS-PAGE: sodium dodecyl sulfate polyacrylamide gel electrophoresis;
PBS: phosphate-buffered saline;
CAAX: tetrapeptides where C is cysteine, A is an aliphatic amino acid and X is any amino acid;
4-ABA: 4-aminomethylbenzoic acid;
DTT: dithiothreitol;
FPP: farnesylpyrophosphate;
GGPP: geranylgeranylpyrophosphate.

The compounds of the invention may be prepared using procedures which are conventional in the art. For example, compounds 4 and 5 of FIG. 1 may be prepared by reductive amination of 4-amino-3'-tert.butoxy-carbonyl biphenyl or 4-amino-4'-tert.butoxy carbonyl biphenyl, respectively, with N-Boc-S-trityl cysteinal followed by deprotection with, for example, trifluoroacetic acid and purification.

The invention is illustrated but not limited by the following examples:

EXAMPLE 1

The compound C-4ABA-Met of formula (2) (see FIG. 1) was prepared as described in reference (27). The protected form of the peptidomimetic (2a) was prepared through the reductive amination of 4-aminobenzoyl methionine methyl ester and N-Boc-S-trityl cysteinal in methanol solution containing NaBH$_3$CN and 5% acetic acid. This reaction gave the N-Boc-S-trityl, methyl ester of (2a) with a yield of 65%. The protected peptidomimetic was deesterified by LiOH in THF and then deprotected by trifluoroacetic acid in methylene chloride with two equivalents of triethylsilane to give crude (2a) which was purified by reverse phase HPLC. The biphenyl-based peptidomimetic (8) was prepared by the reductive amination of 4-amino-3'-methyl biphenyl with N-Boc-S-trityl cysteinal, to give the N-Boc-S-trityl derivatives of (8), which was then deprotected by trifluoroacetic acid and purified by reverse phase HPLC. The peptidomimetics (4) and (5) were prepared from the reductive amination of 4-amino-3'-tert.butoxycarbonyl biphenyl and 4-amino-4'-tert.butoxycarbonylbiphenyl, respectively, with N-Boc-S-trityl cysteinal, to give the N-Boc-S-trityl, tert-butyl ester of (4) and (5). Deprotection by trifluoroacetic acid and purification by reverse phase HPLC gave pure (4) and (5).

Synthesis

The basic approach used for the preparation of the compounds of the invention is illustrated in Scheme 1 with the synthesis of compound 4.

Scheme 1
Representative Synthesis of FTase Inhibitors[a]

[a]Reagents: (a) Pd(OAc)$_2$; (b) KMnO$_4$, pyridine/H$_2$O; (c) (1) (COCl)$_2$, (2) tert-butyl alcohol, n-BuLi; (d) (1) H$_2$, Pd/C, (2) N-Boc-S-tritylcysteinal 17, (3) NaB(CN)H$_3$: (e) TFA, Et$_3$SiH.

Scheme 2
Synthesis of Compounds 11 and 12[a]

[a]Reagents: (a) (1) NBS, (2) NaN₃; (b) (1) H₂, Pd/BaSO₄, (2) N-Boc-S-tritylcysteine, isobutyl chloroformate, Et₃N; (c) TFA, Et₃SiH; (d) (1) H₂, Pd/BaSO₄, (2) N-Boc-S-tritylcysteinal, NaB(CN)H₃.

1-Bromo-4-nitrobenzene was coupled to 3-methylphenylboronic acid (34) through an modified Suzuki coupling (30) to afford compound 14 (35). Compound 14 was oxidized to carboxylic acid 15 which was converted to the acid chloride and reacted with lithium tert-butoxide (36) to give the tert-butyl ester 16. Reduction of 16 by hydrogenation and subseqent reductive amination (37) of the resulting amine with N-Boc-S-trityl-cysteinal 17 (38) gave the fully protected derivative 18, which was deprotected by trifluoroacetic acid in the presence of triethylsilane (39). Compound 4 was purified by reverse phase HPLC and isolated as its trifluoroacetate salt by lyophilization.

The synthesis of 11 and 12 is described in Scheme 2. Compound 19 was made from 3-methyl-3'-carboxybiphenyl (itself formed from aryl-aryl coupling of methyl 3-bromobenzoate with 3-methylphenylboronic acid followed by a saponification) via the same method as compound 16. Bromination of 19 followed by reaction with sodium azide gave 20 which as catalytically hydrogenated to give the corresponding amine. Reaction of Boc-trityl protected cysteine with this amine through the mixed anhydride method gave 21, while compound 22 was made by reductive amination with Boc-trityl protected cysteinal.

Experimental

¹H and ¹³C NMR spectrum were recorded on a Bruker AM-300 spectrometer. Chemical shifts were reported in δ (ppm) relative to tetramethylsilane. All coupling constants were described in Hz. Elemental analyses were performed by Atlantic Microlab Inc., Georgia. Optical rotations were measured on a Perkin-Elmer 241 polarimeter. Concentrations are expressed in g/mL. Flash column chromatography was performed on silica gel (40–63 μm) under a pressure about 4 psi. Solvents were obtained from commercial suppliers and purified as following: tetrahydrofuran and ether were distilled from sodium benzophenone ketyl, methylene chloride was distilled over lithium aluminum hydride. Preparative HPLC was performed using a Waters 600 E controller and a Waters 490 E Multi-Wavelength UV detector with a 25×10 cm Delta-Pak C-18 300 Å cartridge column inside a Waters 25×10 cm Radial Compression Module.

Analytical HPLC was performed using a Rainin HP Controller and a Rainin UV-C detector with a Rainin 250×4.6 mm 5 μm Microsorb C-18 column. High resolution mass spectra (HRMS) and low resolution mass spectra (LRMS) were performed on a Varian MAT CH-5 and VG 7070 mass spectrometer. The purity of all the synthesized inhibitors was more than 98% as indicated by analytical HPLC.

4-Nitro-3'-methylbiphenyl (14). To a mixture of 4-nitrobenzene (3.0 g, 14.8 mmol) and 3-methylphenylboronic acid (2.06 g, 15.1 mmol) in 35 mL of acetone and 40 mL of water was added $K_2CO_3 \cdot 1.5H_2O$ (5.93 g, 37.5 mmol) and $Pd(OAc)_2$ (101 mg, 0.50 mmol). The deep black mixture was refluxed for 6 hr and then cooled. The mixture was extracted with ether and the organic layer was passed through a layer of celite. The pale yellow solution was dried over $Na_2SO_4$ and evaporated to dryness. The residue was recrystallized from hot methanol to give pale yellow crystals (2.68 g, 85%). m.p.59–60° C. $^1$H NMR ($CDCl_3$) δ 8.26 (d, 8.7 Hz, 2H), 7.70 (d, 8.7 Hz, 2H), 7.41 (m, 3H), 7.26 (d, 7.1 Hz, 1H), 2.43 (s, 1H). $^{13}$C NMR ($CDCl_3$) δ 147.6, 146.8, 138.8, 138.6, 129.6, 128.9, 128.0, 127.6, 124.4, 123.9, 21.4. LRMS (EI) for $C_{13}H_{11}NO_2$ 213 ($M^+$, intensity 100); HRMS (EI) calcd 213.0789, obsd 213.0778.

4-Nitro-3'-carboxybiphenyl (15). Compound 14 (2.31 g, 10 mmol) was suspended in a mixture of 10 mL of pyridine and 20 mL of water. The mixture was heated to refluxing and then $KMnO_4$ (7.9 g, 50 mmol) was added in portions. This mixture was refluxed for 1 hr and then stirred at room temperature for 4 hr. The hot mixture was filtered and the black solid was washed with hot water. The filtrate was acidified with 6 N HCl. The precipitate was collected and dried (2.16 g, 89%). m.p. 265° C. (decomp). $^1$H NMR (DMSO-$d_6$) δ 11.1–11.4 (br s, COOH), 8.32 (d, 8.7 Hz, 2H), 8.27 (s, 1H), 8.02 (m, 4H), 7.66 (t, 7.8 Hz, 1H). $^{13}$C NMR (DMSO-$d_6$) δ 167.1, 148.9, 145.6, 138.2, 131.8, 131.5, 129.6 (br), 127.9, 124.2 (br). LRMS (EI) for $C_{13}H_9O_4N$ 243 ($M^+$, 100), 152 (60); HRMS (EI) calcd 243.0531, obsd 243.0544. Anal. ($C_{13}H_9NO_4$) C, H, N.

4-Nitro-3'-tert-butoxycarbonylbiphenyl (16). To a solution of 15 (1.215 g, 5 mmol) in 30 mL of methylene chloride was added oxalyl chloride (0.65 mL, 7.45 mmol) and one drop of DMF. The mixture was stirred until no further bubbling was observed. The clear solution was exaporated to dryness to give the crude acid chloride. To another flask containing 7.0 mL of tert-butanol was added n-BuLi (1.8 M in hexane, 2.8 mL, 5.04 mmol) under a water bath. The turbid solution was stirred for 5 min at room temperature and then the above acid chloride in 20 mL of THF was added through a dropping funnel. The mixture was stirred overnight before the solvents were evaporated. The residue was dissolved into methylene chloride and washed with 0.5 N NaOH. The organic layer was dried over $MgSO_4$ and evaporated. The residue was recrystallized from methanol to give pale yellow crystals (851 mg, 57%). m.p. 110.5–111.0° C. $^1$H NMR ($CDCl_3$) δ 8.32 (d, 7.8 Hz, 2H), 8.24 (s, 1H), 8.06 (d, 7.7 Hz, 1H), 7.77 (m, 3H), 7.56 (t, 7.7 Hz, 1H), 1.63 (s, 9H). $^{13}$C NMR ($CDCl_3$) δ 165.1, 147.1, 146.5, 138.7, 132.8, 131.0, 129.6, 129.0, 128.2, 127.8, 124.0, 81.4, 28.0, LRMS (EI) for $C_{17}H_{17}O_4N$ 299 ($M^+$, 20), 243 (70), 266 (30), 152 (25; HRMS (EI) calcd 299.1157, obsd 299.1192. Anal. ($C_{17}H_{17}NO_4$) C, H, N.

N-Boc-S-trityl cysteinal (17). To a solution of N-Boc-S-trityl cysteine (7.44 g, 16 mmol) in 85 mL of methylene chloride was added triethylamine (2.22 mL, 16 mmoL) and N,O-dimethylhydroxylamine hydrochloride (1.57 g, 16.1 mmol). This mixture was cooled in an ice bath and 1-(3-dimethylaminopropyl)-3-ethylcarbodiimide hydrochloride (EDCI, 3.08 g, 16.0 mmol) and HOBT (2.17 g, 16 mmol) was added. The mixture was stirred at 0° C. for 1 hr and at room temperature for a further 10 hr. The mixture was extracted with methylene chloride and 0.5 N HCl. The organic layer was washed consecutively with 0.5 N HCl, concentrated $NaHCO_3$ and brine. The organic layer was dried and evaporated. The residue was purified by flash column chromatography (1.5:1=hexane:ethylacetate) to give a white foam (7.40 g, 91%). m.p.59–60° (decomp). $^1$H NMR ($CDCl_3$) δ 7.41 (m, 6H), 7.20–7.31 (m, 9H), 5.13 (d, 8.9 Hz, 1H), 4.76 (br s, 1H), 3.64 (s, 3H), 3.15 (s, 3H), 2.56 (dd, 4.7 and 12.1 Hz, 1H), 2.39 (dd, 7.8 and 12.1 Hz, 1H), 1.43 (s, 9H). $^{13}$C NMR ($CDCl_3$ δ 170.7, 154.9, 144.2, 129.3, 127.6, 126.4, 79.3, 66.4, 61.2, 49.5, 33.8, 31.8, 28.1. This carboxyamide (2.02 g, 4.0 mmol) was dissolved in 30 mL of ether and cooled to –10° C. Lithium aluminum hydride (167 mg, 4.40 mmol) was added and the mixture was stirred for 15 min under the nitrogen. Then 40 mL of 0.5 N HCl was added and the solution was extracted with ether. The ether layer was washed with 0.5 N HCl and dried. The evaporation of solvents gave a white foam (1.80 g) which was used for further reaction without purification. The $^1$H NMR spectrum of this compound was complex. The percentage of the aldehyde was about 65–70%, which was calculated according to the integration of the sharp singlet (δ 9.17) and the trityl peak (δ 7.40, m, 6H;7.28,m,9H). Lowering the temperature to –45° C. did not improve the aldehyde percentage.

4-N-[2(R)-tert-butoxycarbonylamino-3-triphenylmethylthipropyl]amino-3'-tert butoxycarbonylibiphenyl (18). Compound 16 (768 mg, 2.56 mmol) was dissolved in THF. A catalytic amount of 10% Pd on activated carbon (78 mg) was added. The mixture was hydrogenated (40 psi) for 30 min. The black mixture was passed throug a thin layer of celite and the pale yellow solution was evaporated. The residue was dissolved in 10 mL of methanol. To this solution was added 0.5 mL of acetic acid and a solution of the same equivalents of aldehyde 17 (according to the $^1$H NMR determination) in 6 mL of methanol. Sodium cyanoborohydride (241 mg, 3.84 mmol, 1.5 eq) was added and the mixture was stirred overnight. After the evaporation of solvents, the residue was extracted with ethyl acetate and concentrated sodium bicarbonate. The organic layer was dried and evaporated. The residue was purified by flash column chromatography (3.5:1-hexane:THF) to give a white foam (1.09 g, 61%). m.p. 75.0–76.0° C. (decomp). $[\alpha]^{25}_D$=–2.13 (c=0.01, $CH_3COOC_2H_5$). $^1$H NMR ($CDCl_3$) δ 8.14 (s, 1H), 7.86 (d, 7.7 Hz, 1H), 7.66 (d, 7.8 Hz, 1H), 7.40 (m, 9H), 7.22–7.30 (m, 9H), 6.61 (d, 8.5 Hz, 2H), 4.58 (d, 7.1 Hz, 1H), 3.83 (br m, 2H, Cys a proton and the amine), 3.12 (br m, 2H, $CH_2N$), 2.48 (br, m, 2H, $CH_2S$), 1.60 (s, 9H), 1.44 (s, 9H). $^{13}$C NMR ($CDcl_3$) δ 165.9, 155.6, 147.5, 144.4, 141.2, 132.3, 130.1, 129.5, 129.2, 128.5, 128.0, 127.9, 127.1, 126.8, 112.9, 80.9, 79.7, 67.0, 49.4, 47.1, 34.3, 28.3, 28.2 (expect 14 aromatic C, observed 13). Anal. ($C_{44}H_{48}N_2O_4S \cdot 1.2H_2O$) C, H, N, S.

4-N-[2(R)-amino-3-mercaptopropyl]amino-3'-carboxybiphenyl (4). Compound 18 (600 mg, 0.85 mmol) was dissolved in 2 mL of TFA and 2 mL of methylene chloride. Triethylsilane was added dropwise to the deep brown mixture until the brown color had disappeared. The mixture was then kept at room temperature for 1 hr. Then solvents were evaporatee and the residue was dried under vacuum. The solid was triturated with 30 mL of ether and 3 mL of 3 N Hcl in ether. The white precipitate was filtered and washed with ether to obtain a crude product (270 mg, 84%). This crude product was dissolved into 30 mL of dilute Hcl solution (0.01 N) and was lyophilized. Analytical HPLC showed the purity to be 95%.m.p. 105–106° C. (decomp). $[\alpha]^{25}{}_D$=+13.16 (c=0.01 in methanol. $^1$J M<R (CD$_3$OD δ 8.18 (s, 1H), 7.89 (d, 7.7 Hz, 1H), 7.78 (d, 7.3 Hz, 1H), 7.49 (m, 3H), 6.82 (d, 8.5 Hz, 2H), 3.56 (m, 2H CHN and CH$_2$N), 3.42 (dd, 8.9 and 15.2 Hz, 1H, CH$_2$S). $^{13}$C NMR (D$_2$O and CD$_3$OD) δ 171.1, 147.1, 141.4, 131.9, 130.9, 130.1, 128.8, 128.5, 127.0, 115.2, 53.2, 45.4, 25.0 LRMS (FAB, glycerol) for C$_{16}$H$_{18}$N$_2$O$_2$S (M+1) 303. Anal. (C$_{16}$H$_{18}$N$_2$O$_2$S.2HCl) C, H, N, S. Further purification by preparative HPLC (Waters C-18, 40% acetonitrile, 60% water, 0.1% TFA, 40 min gradient) gave product 4 (120 mg) with a purity over 99.9%.

3-Methyl-3'-tert-butoxycarbonylbiphenyl (19). The coupling of 3-methylphenylboronic acid with 3-bromobenzoic acid methyl ester gave a 3-methyl-3'-methoxycarbonylbiphenyl (79% yield), which was then hydrolyzed to [[vie a 3-methyl-3'-carboxybiphenyl (97% yield). Compound 19 (an oil) was prepared from this acid using the same method as for the preparation of compound 16 (65% yield). $^1$H NMR (CDl$_3$) δ 8.21 (s, 1H), 7.95 (d, 7.8 Hz, 1H), 7.73 (d, 6.6 Hz), 1H), 7.46 (m, 3H), 7.35 (t, 7.5 Hz, 1H), 7.20 (d, 7.4 Hz, 1H), 2.43 (s, 3H), 1.62 (s, 9H). $^{13}$C NMR (CDCl$_3$) δ 165.6, 141.3, 140.2, 138.3, 132.4, 140.0, 128.7, 128.5, 128.3, 128.0, 127.9, 124.2, 81.0, 28.1, 21.4. LRMS (EI) for C$_{18}$H$_{20}$O$_2$ 268 (M$^+$, 35), 212(100), 195 (20); HRMS (EI) calcd 268.1463, obsd 268.1458.

3-Azido-3'-tert-butoxycarbonylbiphenyl (20). Compound 19 (2.18 g, 8.13 mmol) and N-bromosuccinimide (1.70 g, 9.50 mmol) was suspended in 60 mL of CCl$_4$. Dibenzoyl peroxide (20 mg) was added and the mixture was refluxed for 1.5 hr. After removing the solid, the filtrate was washed with concentrated sodium bicarbonate and dried over sodium sulfate. $^1$H NMR showed the crude material contained 70% of monobrominated and 30% of dibrominated product. This material was dissolved in 20 mL of DMSO and sodium azide (3.70 g, 57 mmol) was added. The mixture was heated to 80° C. for 4 hr before being poured into a mixture of methylene chloride and water. The organic layer was dried and evaporated. The residue was purified by flash column chromatography (5% of ethyl acetate in hexane) to give 20 (2.14 g, 78%, two steps) as colorless oil. $^1$H NMR (CDCl$_3$) δ 8.22 (s, 1H), 8.00 (d, 7.7 Hz, 1H), 7.76 (d, 8.2 Hz, 1H), 7.58 (m, 2H), 7.50 (m, 2H), 7.33 (d, 7.6 Hz, 1H), 4.43 (s, 2H), 1.62 (s, 9H). $^{13}$C NMR (CDCl$_3$) δ 165.2, 140.5, 140.3, 135.8, 132.3, 130.7, 129.1, 128.5, 128.2, 127.8, 127.1, 126.7, 126.6, 80.9, 54.3, 27.8.

N-Boc-S-trityl-cysteinyl-3-aminomethyl-3'-tert-butoxycarbonylbiphenyl (21). Compound 20 (0.75 g, 2.43 mmol) was dissolved in 30 mL of methanol. A catalytic amount of 5% palladium on barium sulfate (0.30 g) was added. The mixture was hydrogenated at 1 atm for 5 hr. The catalyst was removed by filtration and the methanol was evaporated. This residue was dissolved in 40 mL of methylene chloride. N-Boc-S-trityl cysteine (1.12 g, 2.43 mmol) was added at 0° C. followed by EDCI (1 eq) and HOBT (1 eq). The mixture was stirred for 24 hr. After workup and evaporation of solvents, the residue was purified by flash column chromatography (hexane:ethyl acetate=3.2:1) to give 21 (570 mg, 44%). m.p. 84–86° C. $^1$H NMR (CDCl$_3$) δ 8.17 (s, 1H), 7.95 (d, 7.7 Hz, 1H), 7.70 (d, 7.7 Hz, 1H), 7.50–7.30 (m, 9H), 7.30–7.10 (m, 11H), 6.44 (br, 1H), 4.86 (br, 1H), 4.45 (d, 4.0 Hz, 2H, CH$_2$Ph), 3.87 (br, 1H, Cys α H), 2.75 (dd, 7.2 and 12.8 Hz, 1H, CH$_2$S), 2.55 (dd, 5.3 and 12.8 Hz, 1H, CH$_2$S), 1.62 (s, 9H), 1.36 (s, 9H). Anal. (C$_{45}$H$_{48}$N$_2$O$_5$S) C, H, N, S.

Cysteinyl-3-aminomethyl-3'-carboxybiphenyl (11). Compound 21 (150 mg) was deprotected using the same method as for the preparation of compound 4. Final purification by preparative HPLC gave 11 as a white solid (42 mg, 46%). m.p. 88–89° C. (decomp). 1H MNR (CD$_3$OD) δ 8.26 (s, 1H), 8.01 (d, 7.7 Hz, 1H), 7.86 (d, 7.7 Hz, 1H), 7.64 (s, 1H), 7.56 (m, 2H), 7.46 (t, 7.6 Hz, 1H), 7.35 (d, 7.6 Hz, 1H), 4.53 (s, 2H), 4.00 (t, 5.2 Hz, 1H, Cys α H), 3.06 (dd, 14.6 and 5.2 Hz, 1H, CH$_2$S), 2.97 (dd, 14.6 and 6.8 Hz, 1H, CH$_2$S). LRMS (EI) for C$_{17}$H$_{18}$N$_2$O$_3$S 331 (M+1, 8), 281 (100), 226 (75), Anal. (C$_{17}$H$_{18}$N$_2$O$_3$S.HCl.0.6H$_2$O) C, H, N.

3-N-[2(R)-tert-Butoxycarbonylamino-3-triphenylmethylthiopropyl]aminomethyl-3'-tert-butoxy-carbonylbiphenyl (22). The azide 20 (900 mg, 2.91 mmol) was dissolved in 20 mL of methanol. A catalytic amount of 5% Pd on barium sulfate (90 mg) was added. This mixture was hydrogenated at 1 atm overnight. The catalyst was removed and the methanol was evaporated. The remaining residue was dissolved in a mixture of 0.5 N HCl (20 mL) and ether (20 mL). The aqueous phase was neutralized with 1 N NaOH and extracted into methylene chloride. After the evaporation of solvents, a viscous oil was obtain ed (600 mg, 73%). $^1$H NMR (CDCl$_3$) δ 8.22 (s, 1H), 7.97 (d, 7.8 Hz, 1H), 7.75 (d, 7.7 Hz, 1H), 7.57 (s, 1H), 7.50 (m, 2H), 7.43 (t, 7.7 Hz, 1H), 7.33 (d, 7.4 Hz, 1H), 3.96 (s, 2H), 1.62 (s, 9H), 1.46 (br s, 2H, NH$_2$). This amine (581 mg, 2.05 mmol) was dissolved in 10 mL of methanol and 0.5 mL of acetic acid before N-Boc-S-tritylcysteinal (1 eq, according to $^1$H NMR determination of the aldehyde percentage) was added. Sodium cyanoborohydride (193 mg, 1.50 eq) was added to the above solution and the mixture was stirred at room temperature overnight. After workup, the crude residue was purified by flash column chromatography (1:1=ethyl acetate:hexane) to give a white foam (602 mg, 41%). m.p. 66–68° C. (decomp). $^1$H NMR (CDCl$_3$) δ 8.21 (d, 1H), 7.96 (d, 7.7 Hz, 1H), 7.73 (d, 8.0 Hz, 1H), 7.37–7.51 (m, 10H), 7.15–7.31 (m, 10H), 4.69 (br d, 1H), 3.75 (br s, 3H, PhCH$_2$N and Cys α H), 2.68 (dd, 6.0 and 12.3 Hz, 1H, CH$_2$S), 2.56 (dd, 5.5 and 12.3 Hz, 1H, CH$_2$S), 2.47 (m, 1H, CH$_2$N), 2.35 (m, 1H, CH$_2$N), 1.62 (s, 9H), 1.42 (s, 9H) 1.12 (br s, 1H, NH).

3-N-[2(R)-amino-3-mercaptopropyl]aminomethyl-3'-carboxybiphenyl (12). Compound 22 (480 mg, 0.672 mmol) was dissolved in a mixture of 2 mL of methylene chloride and 2 mL of trifluoroacetic acid. Several drops of triethylsilane were added until the deep brown color had disappeared. This mixture was kept at room temperature for 1.5 hr, and then the solvents were evaporated, and the residue was dried under vacuum. The solid residue was dissolved in 1 mL of acetic acid and 2 mL of HCl (1.7 M) in acetic acid. Finally 5 mL of HCl (3 M) in ether and 10 mL of ether were added. The white precipitate was washed with dry ether and dried to give a hydrochloride salt (215 mg, 81%). $^1$H NMR (D$_2$O) δ 8.16 (s, 1H), 7.94 (d, 7.7 Hz, 1H), 7.85 (d, 7.7 Hz, 1H), 7.70 (s, 2H), 7.55 (t, 7.8 Hz, 2H), 7.46 (d, 7.5 Hz, 1H), 4.36 (s, 2H, PhCH$_2$), 3.81 (m, 1H, Cys α H), 3.57 (dd, 5.7 and 13.7 Hz, 1H, CH$_2$N), 3.44 (dd, 6.5 and 13.7 Hz, 1H, CH$_2$N), 2.97 (dd, 5.3 and 15.1 Hz, 1H, CH$_2$S), 2.86 (dd, 5.9 and 15.1 Hz, 1H, CH$_2$S).

2-Methoxy-4-nitro-3'-tert-butoxycarbonylbiphenyl (23). The coupling of 1-bromo-2-methoxy-4-nitrobenzene with 3-methylphenylboronic acid followed by the oxidation gave the 2-methoxy-4-nitro-3'-carboxybiphenyl. The reaction of acid chloride with lithium tert-butoxide gave 23 (3 steps, 35%). m.p. 88.0–88.5° C. $^1$H NMR (CDCl$_3$) δ 8.13 (s, 1H), 8.00 (d, 7.7 Hz, 1H), 7.89 (d, 8.3 Hz, 1H), 7.81 (s, 1H), 7.69 (d, 7.7 Hz, 1H), 7.48 (m, 2H), 3.90 (s, 3H), 1.60 (s, 9H). $^{13}$C NMR (CDCl$_3$) δ 165.2, 156.7, 148.0, 136.3, 136.2, 133.2, 132.0, 130.8, 130.1, 129.0, 127.9, 115.8, 106.0, 81.1, 55.9, 27.9. LRMS (EI) for C$_{18}$H$_{19}$NO$_5$ 329 (M$^+$, 30), 273 (100).

2-Methoxy-4-N-[2(R)-N-tert-butoxycarbonylamino-3-triphenylmethylthiopropyl]amino-3'-tert-butoxycarbonylbiphenyl (24). Compound 24 was prepared using the same method as for the preparation of compound 18 (yield 63%). m.p. 76.0–77.0° C. (decomp). [α]$^{25}$D=−11.25 (c=0.01, CH$_3$COOC$_2$H$_5$). $^1$H NMR (CDCl$_3$) δ 8.09 (s, 1H), 7.86 (d, 7.0 Hz, 1H), 7.65 (d, 7.0 Hz, 1H), 7.37 (t, 7.7 Hz, 1H), 7.43 (m, 6H), 7.21–7.32 (m, 9H), 7.11 (d, 8.1 Hz, 1H), 6.21 (s, 1H), 6.18 (d, 8.1 Hz, 1H), 4.58 (d, 6.1 Hz, 1H), 3.86 (br s, 1H), 3.76 (s and m, 4H), 3.14 (br d, 4.9 Hz, 2H), 2.49 (br d, 5.1 Hz, 2H), 1.59 (s, 9H), 1.43 (s, 9H). $^{13}$C NMR (CDCl$_3$) δ 165.9, 157.3, 155.5, 148.8, 144.3, 138.9, 133.3, 131.5, 131.2, 130.0, 129.4, 127.8, 127.5, 126.7, 118.7, 104.7, 96.2, 80.5, 79.4, 66.8, 55.2, 49.3, 47.0, 34.1, 28.2, 28.1. Anal. (C$_{45}$H$_{50}$N$_2$O$_5$S) C, H, N, S.

2-Methoxy-4-N-[2(R)-amino-3-mercaptopropyl]amino-3'-carboxybiphenyl (10). Compound 10 was obtained from the deprotection of compound 24. m.p. 120–121° C. (decomp). [α]$^{25}$D=+12.62 (c=0.01, in methanol). $^1$H NMR (CD$_3$OD) δ 8.09 (s, 1H), 7.89 (d, 7.8 Hz, 1H), 7.67 (d, 7.8 Hz, 1H), 7.43 (t, 7.7 Hz, 1H), 7.20 (d, 8.1 Hz, 1H), 6.56 (s, 1H), 6.53 (d, 8.1 Hz, 1H), 3.81 (s, 3H), 3.60 (m, 2H, Cys α H and CH$_2$N), 3.48 (m, 1H, CH$_2$N), 2.96 (dd, 4.9 and 13.7 Hz, 1H, CH$_2$S), 2.86 (dd, 5.4 and 13.7 Hz, 1H, CH$_2$S). $^{13}$C NMR (D$_2$O and CD$_3$OD) δ 171.1, 158.2, 149.3, 139.7, 135.1, 132.2, 131.1, 130.4, 129.4, 128.4, 120.5, 106.2 (broad, due to deuterium exchange), 98.8, 56.3, 53.4, 45.1, 24.9. LRMS (EI) for C$_{17}$H$_{20}$N$_2$O$_3$S 332 (M$^+$). Anal. (C$_{17}$H$_{20}$N$_2$O$_3$S.1.2HCl H$_2$O) C, H, N, S.

Cysteinyl-4-amino-3'-carboxybiphenyl (6). Compound 6 was purified through preparative HPLC. Purity was shown to be over 99%. m.p. 120.0–121.0° C. $^1$H NMR (CD$_3$OD) δ 8.25 (s, 1H), 7.98 (d, 7.6 Hz, 1H), 7.84 (d, 7.7 Hz, 1H), 7.74 (d, 7.0 Hz, 2H), 7.54 (t, 7.7 Hz, 1H), 7.66 (d, 8.6 Hz, 2H), 4.16 (q, 5.0 Hz, 1H), 3.19 (dd, 5.20 and 14.8 Hz, 1H), 3.07 (dd, 7.7 and 14.7 Hz, 1H); $^{13}$C NMR (CD$_3$OD) δ 169.8, 166.7, 141.9, 138.7, 137.8, 132.6, 132.2, 130.2, 129.5, 128.8, 128.5, 121.6, 56.9, 26.4. LRMS (E1) for C$_{16}$H$_{16}$O$_3$N$_2$S 316 (M$^+$, 25), 213 (100); HRMS (EI) calcd 316.0882, obsd 316.0867. Anal. (C$_{16}$H$_{16}$N$_2$O$_3$S.CF$_3$COOH.H$_2$O) C, H, N.

4-N-[2(R)-Amino-3-mercaptopropyl]amino-2'-carboxybiphenyl (3). m.p. 129–130° C. (decomp). [α]$^{25}$D=+12.58 (c=0.01, CH$_3$OH). $^1$H NMR (CD$_3$OD) δ 7.73 (d, 7.6 Hz, 1H), 7.50 (d, 7.6 Hz, 1H), 7.35 (m, 2H), 7.21 (d, 8.5 Hz, 2H), 6.86 (d, 8.5 Hz, 2H), 3.58 (m, 2H), 3.46 (m, 1H), 2.97 (dd, 4.8 and 14.6 Hz, 1H), 2.86 (dd, 5.4 and 14.6 Hz, 1H). $^{13}$C NMR (D$_2$O and CD$_3$OD) δ 174.3, 146.3, 141.9, 132.8, 132.7, 131.4, 130.6, 130.2, 127.9, 115.3, 52.9, 45.8, 25.0. LRMS (FAB, glycerol) for C$_{16}$H$_{18}$N$_2$O$_2$S (M+1) 303. Anal. (C$_{16}$H$_{18}$N$_2$O$_2$S.1.6HCl) C, H, N, S.

4-N-[2(R)-Amino-3-mercaptopropyl]amino-4'-carboxybiphenyl (5). m.p. 260° C. (decomp). [α]$^{25}$D=+12.20 (c=0.01, CH$_3$OH). $^1$H NMR (CD$_3$OD) δ 8.03 (d, 8.5 Hz, 2H), 7.66 (d, 8.4 Hz, 2H), 7.56 (d, 8.4 Hz, 2H), 6.85 (d, 8.5 Hz, 2H), 3.57 (m, 2H), 3.45 (m, 1H), 2.98 (dd, 4.8 and 14.5 Hz, 1H), 2.85 (dd, 5.7 and 14.5 Hz, 1H). $^{13}$C NMR (D$_2$O and CD$_3$OO) δ 169.8, 146.4, 146.1, 133.6, 131.4, 129.8, 129.4, 127.1, 117.0, 53.3, 47.2, 25.5. LRMS (EI) for C$_{16}$H$_{18}$O$_2$N$_2$S 302 (M$^+$, 15), 285 (15), 226 (100), 213 (50). HRMS (EI) calcd 302.1088, obsd 302.1089. Anal. (C$_{16}$H$_{18}$N$_2$O$_2$S.2HCl) C, H, N.

4-N-[2(R)Amino-3-Mercaptopropyl]aminobiphenyl (7). m.p. 216° C. (decomp). [α]$^{25}$D=+13.27 (c=0.01, CH$_3$OH). $^1$H NMR (CD$_3$OD) δ 7.54 (m, 4H), 7.39 (m, 2H), 7.26 (m, 1H), 6.82 (br s, 2H), 3.56 (br m, 2H), 3.45 (m, 1H), 2.98 (m, 1H), 2.87 (m, 1H); $^{13}$C NMR (CD$_3$OD) δ 144.8, 141.8, 135.7, 129.9, 129.1, 127.8, 127.4, 117.4, 53.2, 47.6, 25.5. LRMS (EI) for C$_{15}$H$_{18}$N$_2$S 258 (M$^+$, 15), 182 (100); HRMS (EI) calcd 258.1190, obsd 258.1183. Anal. (C$_{15}$H$_{18}$N$_2$S.1.6HCl) C, H, N, S.

4-N-[2(R)-Amino-3-mercaptopropyl]amino-3'-methylbiphenyl (8). $^1$H NMR (CD$_3$OD) δ 7.50 (d, 8.2 Hz, 2H), 7.35 (m, 2H), 7.27 (t, 7.6 Hz, 1H), 7.08 (d, 7.3 Hz, 1H), 6.95 (d, 8.2 Hz, 2H), 3.60 (m, 2H), 3.46 (m, 1H), 2.99 (dd, 4.9 and 14.6 Hz, 1H), 2.88 (dd, 5.5 and 14.6 Hz, 1H), 2.37 (s, 3H). LRMS (EI) for C$_{16}$H$_{20}$N$_2$S 272 (M$^+$, 15), 196 (100). HRMS (EI) calcd 272.1341, obsd 272.1347.

4-N-[2(R)-Amino-3-mercaptopropyl]amino-3'-methoxycarbonylbiphenyl (9). m.p. 86–89° C. (decomp). $^1$H NMR (CD$_3$OD) δ 8.18 (s, 1H), 7.90 (d, 7.7 Hz, 1H), 7.79 (d, 6.6 Hz, 1H), 7.55 (d, 8.6 Hz, 2H), 7.49 (t, 7.7 Hz, 1H), 7.01 (d, 8.6 Hz, 2H), 3.92 (s, 3H), 3.543.65 (m, 2H), 3.44–3.52 (m, 1H), 2.97 (dd, 4.7 and 14.7 Hz, 1H), 2.88 (dd, 5.5 and 14.7 Hz, 1H). LRMS (EI) for C$_{17}$H$_{20}$O$_2$N$_2$S 316 (M+, 15), 299 (20), 240 (100). HRMS (EI) calcd 316.1240, obsd 316.1239. Anal. (C$_{17}$H$_{20}$N$_2$O$_2$S.2HCl) C, H, N, S.

TABLE 1

Table of Microanalysis Data

| Compd | Formulae | C %(cal, obs) | H %(cal, obs) | N %(cal, obs) | S %(cal, obs) |
|---|---|---|---|---|---|
| 3 | C$_{16}$H$_{18}$N$_2$O$_2$S.1.6HCl | 53.27(53.41) | 5.44(5.78) | 7.77(7.35) | 8.87(8.47) |
| 4 | C$_{16}$H$_{18}$N$_2$O$_2$S.2HCl | 51.20(51.60) | 5.37(5.30) | 7.47(7.07) | 8.53(8.22) |
| 5 | C$_{16}$H$_{18}$N$_2$O$_2$S.2HCl | 51.20(51.62) | 5.37(5.56) | 7.47(7.00) | |
| 6 | C$_{16}$H$_{16}$N$_2$O$_3$S.CF$_3$COOH.H$_2$O | 48.21(48.24) | 4.24(4.20) | 6.25(6.32) | |
| 7 | C$_{15}$H$_{18}$N$_2$S.1.6HCl | 56.89(57.04) | 6.19(6.46) | 8.85(8.74) | 10.11(10.03) |
| 9 | C$_{17}$H$_{20}$N$_2$O$_2$S.2HCl | 52.44(52.84) | 5.65(5.92) | 7.19(7.37) | 8.22(8.53) |
| 10 | C$_{17}$H$_{20}$O$_3$S.2HCl.H$_2$O | 51.80(51.91) | 5.89(5.96) | 7.11(6.81) | 8.12(7.77) |
| 11 | C$_{17}$H$_{18}$N$_2$O$_3$S.HCl.0.6H$_2$O | 54.07(54.11) | 5.35(5.39) | 7.42(7.35) | |
| 15 | C$_{13}$H$_9$NO$_4$ | 64.19(64.05) | 3.70(3.75) | 5.76(5.80) | |
| 16 | C$_{17}$H$_{17}$NO$_4$ | 68.23(68.07) | 5.68(5.73) | 4.68(4.64) | |
| 18 | C$_{44}$H$_{48}$N$_2$O$_4$S.1.2H$_2$O | 73.17(72.82) | 6.98(6.83) | 3.88(3.87) | 4.43(4.50) |
| 21 | C$_{45}$H$_{48}$N$_2$O$_5$S | 74.14(73.74) | 6.64(6.74) | 3.84(3.79) | 4.39(4.32) |
| 24 | C$_{45}$H$_{50}$N$_2$O$_5$S | 73.97(73.72) | 6.85(7.04) | 3.83(3.66) | 4.38(4.32) |

TABLE 2

Examples of Peptidomimetics of the Invention

| Compound | | Structure |
|---|---|---|
| 2 | FTI-232 | Cys-4-aminobenzoyl-Met |
| 2a | FTI-249 | red.Cys-4-aminobenzoyl-Met |
| 3 | FTI-273 | red.Cys-4-amino-2'-carboxybiphenyl |
| 4 | FTI-265 | red.Cys-4-amino-3'-carboxybiphenyl |
| 5 | FTI-271 | red.Cys-4-amino-4'-carboxybiphenyl |
| 6 | FTI-278 | Cys-4-amino-3'-carboxybiphenyl |
| 7 | FTI-268 | red.Cys-4-aminobiphenyl |
| 8 | FTI-263 | red.Cys-4-amino-3'-methylbiphenyl |
| 9 | FTI-259 | red. Cys-4-amino-3'-carboxymethylbiphenyl |
| 10 | FTI-281 | red.Cys-4-amino-2-OMe-3'-carboxybiphenyl |
| 11 | FTI-285 | red.Cys-4-amino-2-phenyl-3'-methylbiphenyl |
| 12 | FTI-238 | Cys-3-aminomethyl-3'-carboxybiphenyl |
| | FTI-283 | red.Cys-3-aminomethyl-3'-carboxybiphenyl |
| | FTI-282 | (DL)4-(2,3-diaminopropyl)-amino-3'carboxybiphenyl |
| | FTI-288 | red.Cys-4-amino-2-OPr-3'-carboxybiphenyl |
| | FTI-289 | red.Cys-4-amino-2-phenyl-3'-carboxybiphenyl |
| | FTI-291 | 4-(3-aminoalanyl)-amino-3'-carboxybiphenyl |
| | FTI-292 | (L)4(2,3-diaminopropyl)-amino-3'-carboxybiphenyl |
| | FTI-295 | 4-(Ethylsulfonyl-3-aminoalanyl)-amino-3'-carboxybiphenyl |
| | FTI-296 | 4-(Vinylsulfonyl-3-aminoalanyl)-amino-3'-carboxybiphenyl |
| | FTI-2102 | red.Cys-4-amino-3'-tetrazolylbiphenyl |

Number designations used for compounds of the invention discussed below is shown in Table 2.

EXAMPLE 2

FTase and GGTase I Activity Assay

Human Burkitt lymphoma (Daudi) cells (ATCC, Rockville, Md.) were grown in suspension in RPMI 1640 medium containing 10% fetal bovine serum (FBS) and 1% Pen-Strep in a humidified 10% $CO_2$ incubator at 37° C. The cells were harvested and sonicated in 50 mM Tris, pH 7.5, 1 mM EDTA, 1 mM EGTA, 25 µg/ml leupeptin, 1 mM phenylmethylsulfonyl fluoride. Homogenates were then spun at 12,000×g and the resulting supernatant further spun at 60,000×g. The supernatant was assayed for both FTase and GGTase I. Briefly, 100 µg of the supernatants was incubated in 50 mM Tris, pH 7.5, 50 µM $ZnCl_2$, 20 mM KCl, 3 mM $MgCl_2$ and 1 mM DTT. For FTase assays, the reaction was incubated at 37° C. for 30 minutes with recombinant H-Ras-CVLS (11 µM) and [$^3$H] FPP (625 nM; 16.3 Ci/mmol). For GGTase assays, the reaction was also incubated for 30 minutes at 37° C. but with recombinant H-Ras-CVLL (5 µM) and [$^3$H] GGPP (525 nM; 19.0 Ci/mmol). The reaction was stopped and passed through glass fiber filters to separate free and incorporated label. For inhibition studies, the peptidomimetics were premixed with FTase or GGTase I prior to adding the remainder of the reaction mixture. Recombinant H-Ras-CVLS was prepared as described previously (26) from bacteria (31). Recombinant H-Ras-CVLL was prepared from bacteria (32).

EXAMPLE 3

Peptidomimetics Farnesylation Assay

The ability of human Burkitt lymphoma (Daudi) FTase to farnesylate peptides and peptidomimetics was determined as described previously (26, 27). Briefly, 25 µl of reaction mixture containing 50 µg of 60,000×g supernatants and 20 µM peptidomimetic in 50 mM Tris, pH 7.5, 50 µM $ZnCl_2$, 20 mM KCl, 3 mM $MgCl_2$, 1 mM DTT and 0.2% octylβ-D-glucoside was incubated for 30 minutes at 37° C., then spotted onto silica gel G TLC sheets (20×20 cm, Brinkmann Instruments), and developed with n-propanol/5 N ammonium hydroxide/water (6:1:1). The dried sheets were sprayed with En$^3$Hance (DuPont NEN) and exposed to x-ray film for detection of [$^3$H] farnesylated products.

EXAMPLE 4

Ras and Rap1A Processing Assay

EJ3 cells were treated with peptidomimetics or vehicle for 20–24 h. Cells were lysed in lysis buffer (10 mM $Na_2HPO_4$, pH 7.25, 150 mM NaCl, 0.1% sodium dodecyl sulfate, 1% Triton X-100, 12 mM sodium deoxycholate, 1 mM NaF, 0.2% $NaN_3$, 2 mM PMSF, 25 µg/ml leupeptin) and the lysates were cleared by spinning at 13,000 rpm for 15 minutes. Ras protein was immunoprecipitated overnight at 4° C. with 50 µg of anti-Ras antibody (Y13-259; hybridoma from ATCC, Rockville, Md.) along with 30 µl Protein A-agarose goat anti-rat IgG complex (Oncogene Science, Uniondale, N.Y.). Immunoprecipitates were washed 4 times with lysis buffer and the bound proteins were released by heating for 5 minutes in 40 µl SDS-PAGE sample buffer and subsequently electrophoresed on a 12.5% SDS-PAGE. Proteins were transferred onto nitrocellulose and subsequently blocked with 5% non-fat dry milk in PBS (containing 1% Tween 20 (PBS-T) and probed with Y13-259 (50 µg/ml in 3% non-fat dry milk in PBS-T). Positive antibody reactions were visualized using peroxidase-conjugated goat anti-rat IgG (Oncogene Science, Uniondale, N.Y.) and an enhanced chemiluminescence detection system (ECL; Amersham).

For Rap1A processing assays, 50 µg of cell lysates were electrophoresed as described above for Ras processing and transferred to nitrocellulose. These membranes were then blocked with 5% milk in Tris-buffered saline, pH 8.0, containing 0.5% Tween-20 and probed with anti-Rap1A (1 µg/ml in 5% milk/TBS-T; Santa Cruz Biotechnology, Santa Cruz, Calif.). Antibody reactions were visualized using peroxidase-conjugated goat anti-rabbit IgG (Oncogene) and ECL chemiluminescence as described above.

Structural Modeling (FIG. 2)

The calculation of the energy minimized conformations was carried out using the AMBER force field within the MacroModel program, version 3.5a.

EXAMPLE 5

The potency of the peptidomimetics of FIG. 1 and Table 2 for inhibiting partially purified FTase was evaluated by determining their ability to inhibit the transfer of farnesyl to recombinant H-Ras as described above. The results are summarized in Table 3, which indicates the $IC_{50}$s obtained for FTase activity and GGTase-I activity, and the selectivity for a number of peptidomimetics of the invention. The $IC_{50}$ values given in Table 3 represent inhibition of FTase and GGTase I in vitro by the listed compounds.

TABLE 3

In vitro Activity of CAAX Mimetic Inhibitors of FTase

| Inhibitor | FTase $IC_{50}$ (nM) | GGTase-I $IC_{50}$ (nM) | Selectivity | Substrate |
|---|---|---|---|---|
| FTI-232 | 150 | 1500 | 10 | |
| FTI-249 | 300 | 4400 | 15 | |
| FTI-273 | 543 (3)[a] | 140,000 (2)[a] | 258 | nd[b] |

TABLE 3-continued

In vitro Activity of CAAX Mimetic Inhibitors of FTase

| Inhibitor | FTase IC$_{50}$ (nM) | GGTase-I IC$_{50}$ (nM) | Selectivity | Substrate |
|---|---|---|---|---|
| FTI-265 | 114 (10) | 100,000 (6) | 877 | no |
| FTI-271 | 4575 (4) | >100,000 (2) | >22 | no |
| FTI-278 | 13,500 (2) | 100,000 (2) | 7 | nd |
| FTI-268 | 1,070 (3) | >100,000 (3) | 93 | no |
| FTI-263 | 710 (3) | >100,000 (3) | 141 | no |
| FTI-259 | 917 (3) | >100,000 (3) | 109 | no |
| FTI-281 | 40 (6) | 43,600 (5) | 1090 | nd |
| FTI-238 | 100,000 (2) | >100,000 (3) | >1 | no |
| FTI-283 | 11,000 (1) | 35,000 (2) | 3 | nd |
| FTI-285 | 2075 (4) | 8500 (2) | 4 | |
| FTI-282 | 50,000 (1) | >>100,000 (1) | >2 | |
| FTI-288 | 41 (6) | 2375 (4) | 59 | |
| FTI-289 | 16 (5) | 643 (4) | 40 | |
| FTI-291 | 210,000 (1) | | 0 | |
| FTI-292 | 60,000 (1) | | 0 | |
| FTI-295 | 200,000 (1) | >1,000,000 (1) | >5 | |
| FTI-296 | 430,000 (1) | >>1,000,000 (1) | >2 | |
| FTI-2102 | 30 (1) | 5,000 (1) | 187 | |

[a]Numbers in parentheses indicate number of determinations. Where no number is given, at least two determinations were made.
[b]nd indicates not determined.

The results obtained showed that compound 2, i.e. Cys-4ABA-Met (1–10 μM) inhibited FTase in a concentration-dependent manner with an IC$_{50}$ of 150 nM (FTI-232, Table 3). This value is similar to the previously reported IC$_{50}$ values for CVIM (SEQ ID NO:1) and Cys-4ABA-Met (27). Reduction of the amide bond between cysteine and aminobenzoic acid gave the red-Cys-4ABA-Met (2a, FTI-249) which had an IC$_{50}$ of 300 nM. However, replacing the methionine and the C-terminal amide bond in (2a) by another aromatic ring to obtain the biphenyl-based peptidomimetic (4) improved potency by twofold (FTI-265, Table 3). Peptidomimetic 4 had an IC$_{50}$ of 114 nM towards partially purified FTase from human Burkitt lymphoma cells and 50 nM towards rat brain FTase purified to homogeneity. Thus, despite major structural differences between the compound CVIM (1) (SEQ ID NO 1) and 4, the latter (4) retained the potent FTase inhibitory activity of the tetrapeptide CVIM (1) and the peptide mimetics 2 and 2a. This is significant because 4, being free of any amide bonds, is significantly less subject to degradation in vivo.

Figure 3A:
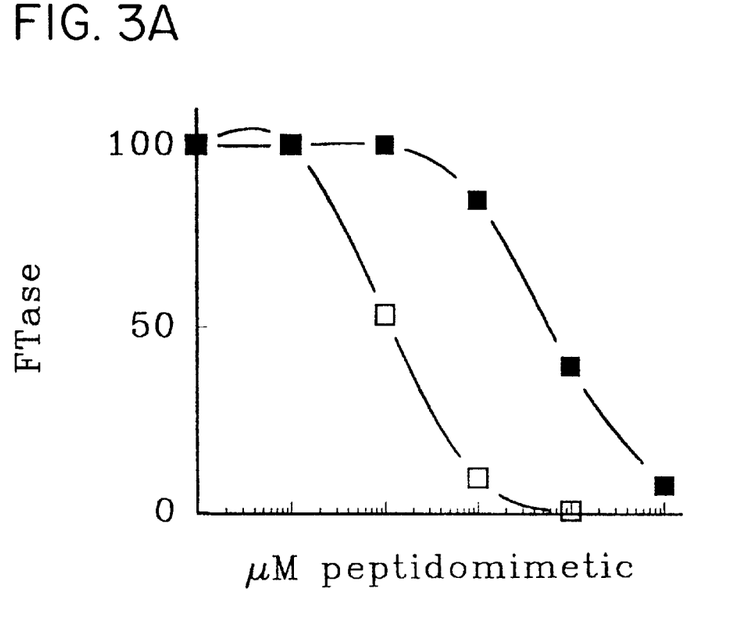
FIGS. 3A and B graphically illustrate the results of FTase and GGTase I inhibition studies.

The results obtained indicate that the position of the free carboxylate group is critical to FTase inhibition since placing this group at the 4'-position as in compound 5 (FIG. 1) dramatically decreased its affinity towards FTase (see FIG. 3A and Table 3). Thus, peptidomimetic 5 (IC$_{50}$=4575 nM) was approximately 40-fold less potent than its isomer 4. This strongly suggests that within the active site of FTase, there must be a positively charged residue such as Lys with a precise spatial orientation to interact with the negative charge of the free carboxylate.

Replacing the 3'-carboxylate of 4 with a methyl group as in 8 also decreased potency but only by about 6-fold (IC$_{50}$=710 nM). This indicates that the FTase binding site prefers a neutral group at the 3'-position to a negative charge at the 4'-position suggesting either steric hindrance or repulsive interactions from the microenvironment surrounding the 4'-region of the biphenyl.

Notwithstanding the lower activity for 5 and 8, these compounds still offer in vivo advantages in view of their freedom from any amide group.

The above results indicate that the tripeptide AAX is not essential for strong binding and all that is required for recognition is a hydrophobic scaffold with free thiol, amino and carboxylate groups held at precise positions. As noted earlier, a previous proposal (29, 33) suggested that potent inhibitory activity towards FTase might require inhibitors to take up a β turn conformation bringing the cysteine thiol and free carboxylate in close proximity to form a bidentate complex with $Zn^{++}$. However, the biphenyl-based non-peptide CAAX mimetic described here cannot take up this conformation (FIG. 2) thus leading to the conclusion that potent inhibition of FTase does not require β turn conformation.

Figure 3B:
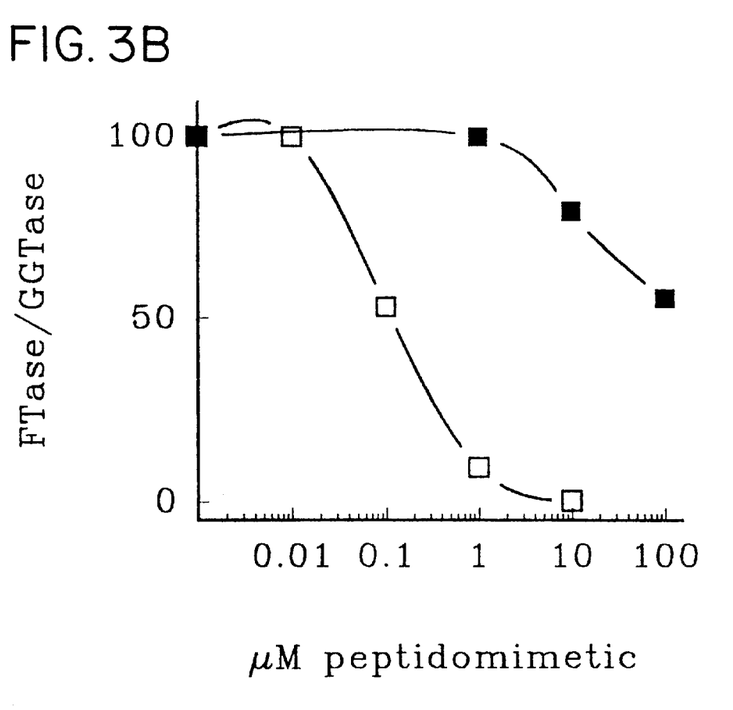

As noted, FIGS. 3A and 3B graphically illustrate the results of FTase and GGTase I inhibition studies. In these studies, partially purified FTase and GGTase I were incubated with the peptidomimetics to be tested and their ability to transfer [$^3$H] farnesyl to H-Ras-CVLS (FTase) and [$^3$H] geranylgeranyl to H-Ras CVLL (CCTase I) was determined as described below. FIG. 3A shows FTase inhibition by: □, (4) and ■, (5) while FIG. 3B plots FTase (□) and GGTase I (■) inhibition by (4). Each curve is representative of at least four independent experiments.

Geranylgeranylation is a more common protein prenylation than farnesylation (15). It is, therefore, desirable for useful CAAX peptidomimetics which are designed to target FTase to have high selectivity towards inhibiting FTase in order to minimize side effects. In the CAAX tetrapeptides, the X position determines whether the cysteine thiol will be farnesylated by FTase or geranylgeranylated by GGTase I. Those proteins or peptides with Leu or Ile at the X position are geranylgeranylated. As shown in Table 3, the present compounds do not significantly inhibit GGTase I and demonstrate much greater selectivity for FTase.

FIG. 3B shows that compound 4, which is a potent FTase inhibitor, is a very poor GGTase I inhibitor. The ability of compound 4 to inhibit the transfer of geranylgeranyl to Ras-CVLL (IC$_{50}$=100,000 nM) was found to be 877-fold less than that of 4 to inhibit the transfer of farnesyl to Ras-CVLS (IC$_=$=114 nM) (Table 3). This selectivity was much more pronounced than in the peptidomimetics 2 and 2a which were more selective for FTase relative to GGTase I by only 10 and 15-fold, respectively. It is also noted that the free carboxylate of compound 4 is not responsible for this selectivity since replacement of this group by a methyl in compound 8 did not increase affinity towards GGTase I (Table 3). These results indicate that the FTase and GGTase I binding sites are quite different and that differences between Leu, Ile and Met side chains cannot be the only predictors of selectivity. Regardless of the explanation, it is clear that the compounds of the invention are much more selective to inhibition of FTase.

Figure 4:
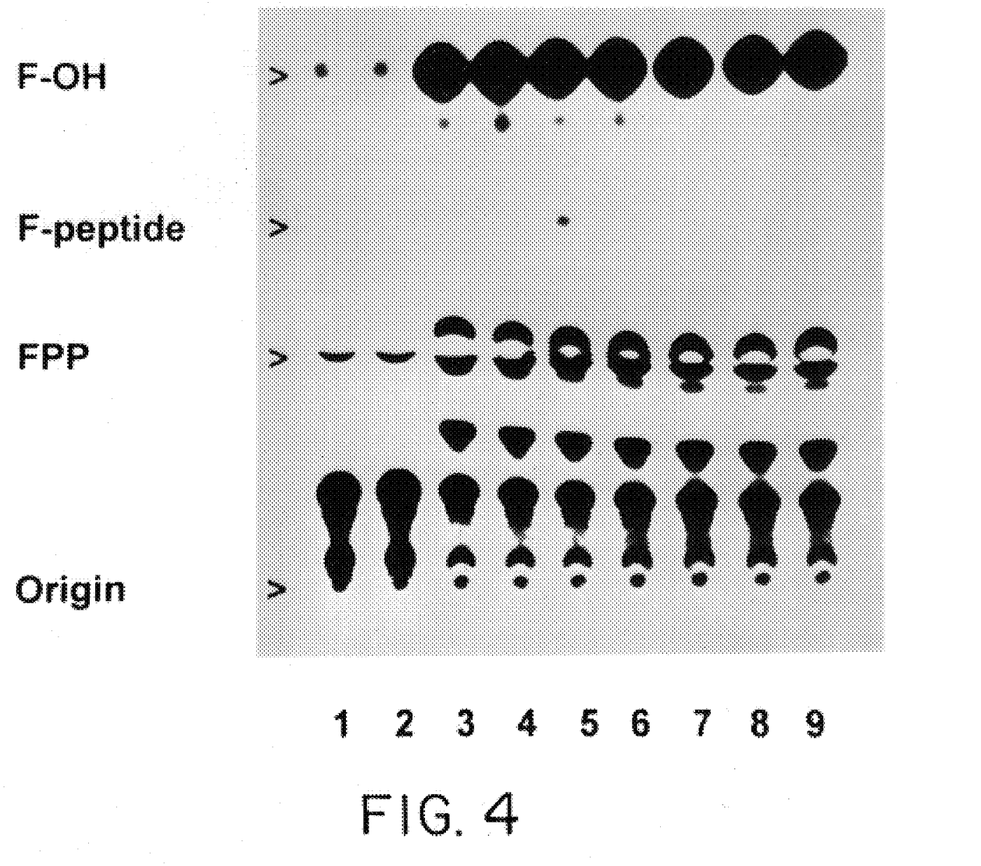
FIG. 4 is a silica gel TLC relating to Ras CAAX peptide and peptidomimetic farnesylation.

Besides having poor cellular uptake and being rapidly degraded, another disadvantage of natural CAAX peptides is that they are farnesylated by FTase. This results in metabolic inactivation since farnesylated CAAX derivatives are no longer inhibitors of FTase (26). FIG. 4 shows that the natural peptide CVLS (SEQ ID NO:2) (carboxyl terminal CAAX of H-Ras) is farnesylated by FTase from Burkitt lymphoma cells. Replacing the tripeptide VLS with 4-amino-3'-hydroxycarbonylbiphenyl, as in 4 did not affect potency towards FTase inhibition (Table 3) but prevented farnesylation of the cysteine thiol (FIG. 4). None of the peptidomimetics of the invention is metabolically-inactivated by FTase (FIG. 4). Thus, although AAX tripeptides are not necessary for potent FTase inhibition, they appear to be required for farnesylation.

With reference to FIG. 4, it is to be noted that the transfer of [$^3$H] farnesyl to peptides and peptidomimetic by FTase was determined by silica G TLC as described below. FPP, F-peptide, and ORIGIN designate farnesyl pyrophosphate, farnesylated peptide and origin, respectively. FIG. 4 shows: Lane 1, FPP only; lane 2, FPP and CVLS (SEQ ID NO:2) but no FTase; lane 3, FPP and FTase but not peptide. Lanes 4–9 all contained FTase and FPP with lane 4, CVIM (SEQ ID NO:1); lane 5, CVLS; lane 6, compound 2a; lane 7, compound 4; lane 8, compound 5; lane 9, compound 8. The results shown indicate that the compounds of the invention are not farnesylated in contrast to the CAAX compounds. Data given are representative of two independent experiments.

Figure 5A:
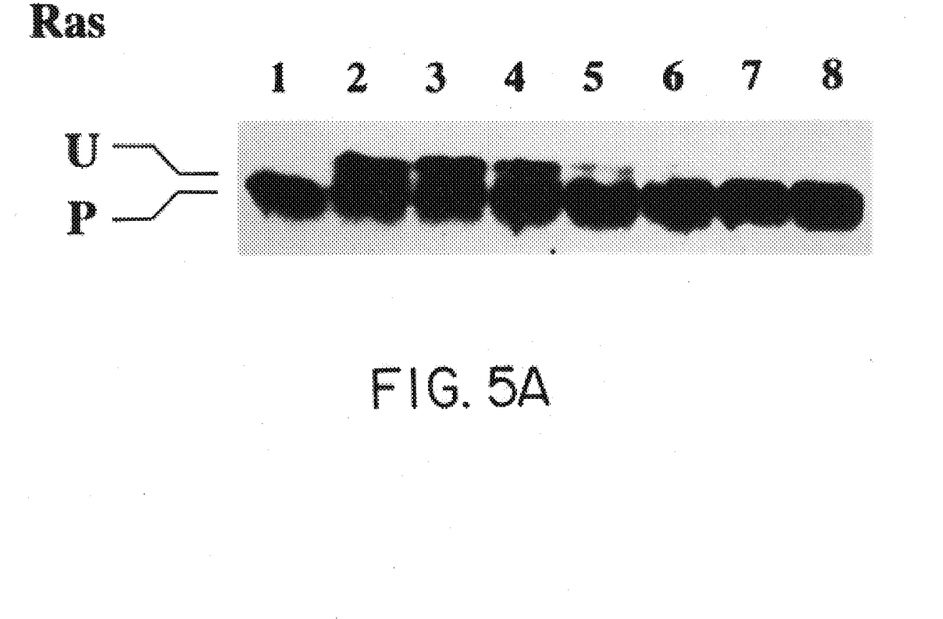
FIG. 5 illustrates Ras and Rap1A processing in cells using a compound according to the invention.

The foregoing results show that the novel peptidomimetics described herein have three very important features, namely, they are potent FTase inhibitors, very poor inhibitors of the closely related GGTase I (and, therefore, selective to FTase inhibition) and they are resistant to metabolic inactivation by FTase. Another important feature is that the present compounds inhibit Ras processing in whole cells and retain their selectivity towards FTase in vivo. This is shown by the following with reference to FIG. 5 which illustrates Ras and Rap1A processing. To this end, Ras transformed 3T3 cells were treated with inhibitors, lysed and the lysate A) immunoprecipitated with anti-Ras antibody or B) separated by SDS-PAGE. Immunoprecipitates from A) were separated by SDS-PAGE and blotted with anti-Ras antibody whereas samples from B) were blotted with anti-Rap1A antibody as described hereafter. FIG. 5 shows: Lane 1, control; lane 2, lovastatin; lane 3, reduced 2a (200 $\mu$M); lane 4, 4 (100 $\mu$M); lane 5, 4 (50 $\mu$M); lane 6, 4 (25 $\mu$M); lane 7, 5; lane 8, 8. Data are representative of 3 independent experiments. Farnesylated Ras runs faster than unprocessed Ras on SDS-PAGE (23–25, 28, 29). FIG. 5A (lane 1) shows that cells treated with vehicle contain only processed Ras whereas cells treated with lovastatin (lane 2) contained both processed and unprocessed Ras indicating that lovastatin inhibited Ras processing. Lovastatin, an HMG-CoA reductase inhibitor which inhibits the biosynthesis of farnesylpyrophosphate and geranylgeranylpyrophosphate, is used routinely as a positive control for inhibition of processing of both geranylgeranylated and farnesylated proteins (23–25, 28, 29). Cells treated with reduced Cys-4ABA-Met 3 in its free carboxylate forms did not inhibit Ras processing. However, in contrast, the corresponding methyl ester of 2a (200 $\mu$M) inhibited FTase (FIG. 5A, lane 3). This is consistent with previous work that showed that neutralization of the carboxylate of CAAX peptides enhances their ability to inhibit Ras processing (23, 25, 29). Although compound 4 has a free carboxylate negative charge, it was able to enter cells and potently inhibit Ras processing (lane 4, 100 $\mu$M compound 4). It was found that compound 4 inhibited Ras processing with concentrations as low as 50 $\mu$M (lane 5), whereas its corresponding parent compound 2a did not inhibit Ras processing at concentrations as high as 200 $\mu$M. Compound 4 was as potent as the methylester of its parent compound (2a) (FIG. 5A, lane 3). Furthermore, 4 appears to be the first CAAX peptidomimetic that effectively inhibits Ras processing in whole cells directly without relying on cellular enzymes for activation. The hydrophobic character of the biphenyl group apparently compensates for the free carboxylate negative charge thus allowing the peptidomimetic to penetrate membranes and promoting its cellular uptake. Peptidomimetics 5 and 8 were not able to inhibit Ras processing (FIG. 5A, lanes 7 and 8).

Figure 5B:
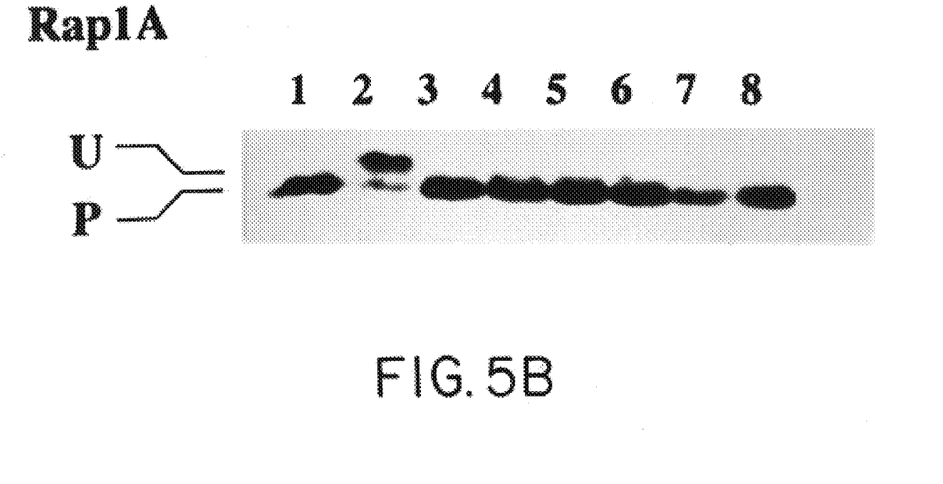

The selectivity of the present Ras farnesylation inhibitors has also been investigated by determining their ability to inhibit processing of Rap1A, a small G-protein that is geranylgeranylated (15, 16). Cells were treated with lovastatin or peptidomimetics exactly as described for Ras processing experiments. Lysates were then separated by SDS-PAGE and immunoblotted with anti-Rap1A antibody as described below. Control cells contained only the geranylgeranylated Rap1A (FIG. 5B, lane 1) whereas lovastatin-treated cells contained both processed and unprocessed forms of Rap1A indicating, as expected, that lovastatin inhibited the processing of Rap1A (FIG. 5B, lane 2). Compound 4, which inhibited Ras processing, was not able to inhibit Rap1A geranylgeranylation (FIG. 5B, lanes 4–6). Compounds 5 and 8 also did not inhibit Rap1A processing (FIG. 5B, lanes 7 and 8).

Structures for a number of compounds of the invention are summarized in Table 2, and their relative effectiveness in inhibiting FTTase and GGTase shown in Table 3. The activity of the inhibitors is reported in Table 3 as $IC_{50}$ values, the concentration at which FTase or GGTase I activity was inhibited by 50%. Some of the inhibitors were further characterized for their ability to serve as substrates for farneylsation by thin layer chromatography, as shown in Table 3 (40).

The published sequence dependence studies on FTase have shown a strong preference for methionine in the terminal position of CAAX. In the compounds of the present invention, no methionine residue is present and the tripeptide AAX is completely replaced by a simple hydrophobic moiety. The most potent inhibitor in the CAAX series is Cys-Ile-Phe-Met (17,20) with an $IC_{50}$ value of 30 nM. Peptidomimetic inhibitor 10 is as potent as CIVM despite the large difference between their structures. These results confirm the hydrophobic strategy for AAX replacement according to the invention.

As seen in Table 3, the precise positioning of the free carboxylate is important for potent inhibition. FTI-273, 265, and 271 (Compounds 3, 4, and 5) differ only in their positioning of the carboxylic acid on the phenyl ring. FTI 265 has the carboxylic acid positioned in correspondence with the dipeptide mimetic 2, while the positioning in 3 and 5 is either closer or farther from the N-terminus. The effect of this changing position on inhibition potency is significant (5 fold difference between 4 and 3, 40 fold difference between 4 and 5).

The influence of different substituents at the 3'-position of compound 4 on FTase inhibitory potency can be seen by comparing compounds 4, 7, 8, and 9. Methylation of the carboxylic acid, as in 9, or replacement of the carboxylic acid by methyl or hydrogen, as in 8 and 7, resulted in inhibitors with 10-fold less activity (approx. 1 $\mu$M) than 4. This suggests that in the active site of the enzyme there is a positively charged residue which interacts with the negatively charged carboxylate at the 3'-position of the aromatic ring. The different activity between 7 and 5 (4 fold) suggested that the 4'-position of the aromatic ring is close to a hydrophobic region in the enzyme.

Probably the most striking result comes from reduction of the amide bond. For tetrapeptide CIFM, it has been shown by others that reduction of the N-terminal peptide bond results in loss of selectivity of FTase over GGTase I, while the reduction of the C-terminal peptide bond leads to a reduction in FTase inhibitory potency (24). In contrast, the compounds of the invention show an unexpected and surprising increase in selectivity for FTase over GGTase I when the cysteine amide bond is reduced (compare 4 to 6). It is also apparent that the C-terminal amide bond is not necessary for potent inhibition activity, since compound 10, which lacks this bond, shows excellent activity.

In an earlier report (40), reduction of the cysteine amide bond of compound 2 had little effect on activity. In contrast, it can be seen in Table 3 that such reduction results in a 100 fold difference in inhibition activity between 4 and 6. One reason for this enhanced activity on reduction of the amide bond is the increased flexibility of the (R)-2-amino-3-mercaptopropyl unit and the consequent accessibility of alternative binding conformations.

The effect of increasing hydrophobicity and restricting conformational flexibility of the biphenyl spacer is demonstrated by placing substituents at the 2-position of the aryl ring. The substitution of hydrogen by a methoxy group at the 2-position of the left hand aromatic ring increased the inhibitory activity by 3 fold. Thus, 2-methoxy-4-N-[2(R)-amino-3-mercaptopropyl]amino-3'-carboxybiphenyl has one of the most potent activities ($IC_{50}$=20–60 nM in 6 independent experiments). This suggested there might be a hydrophobic interaction between the enzyme active site and the methoxy group, corresponding to the valine or isoleucine binding pocket with CVIM (SEQ ID NO 1). This is supported by further studies where substitutions at the 2-position included propoxy (FTI-288) and phenyl (FTI-289) ($IC_{50}$=41 nM and 16 nM, respectively, see Table 3).

In contrast to the dipeptide mimetic in which cysteine and methionine were linked through 3-aminomethylbenzoic acid (26,27,28), the biphenyl derivatives of compound 11 and 12 have extremely poor activity toward FTase even though they retain a similar distance dependence when compared with compound 4. This result suggested that the pharmacophore of (R)-1,2-diamino-3-mercaptopropane must be linked to a well defined hydrophobic residue in order to obtain a potent inhibition activity.

As previously reported, the incorporation of an aromatic amino acid into the $A_2$ position of $CA_1A_2X$ (such as CIFM) prevents the tetrapeptide from serving as a substrate for farneyslation (20). Table 3 shows that the designed non-peptide CAAX mimetics (such as compound 4) are not substrates for farnesylation. This lack of farnesylation by FTase may be due to the inhibitor binding to the enzyme in a conformation that does not permit farnesyl transfer to the thiol group.

Since GGTase is an enzyme closely related to FTase, and geranylgeranylation is a more common protein prenylation reaction than farnesylation (15), it is critical for FTase inhibitors to be selective. The results from Table 3 demonstrate that the compounds of the invention are poor inhibitors of GGTase I. The selectivity for FTase over GGTase I with compound 10 is about 1100 fold. In the tetrapeptide CAAX series, the X position directs farnesylation or geranylgeranylation. Despite removing all features of the CAAX C-terminal residue (Met or Ser) from these peptidomimetics, the high selectivity against GGTase I is retained. This suggests there is a larger difference than previously thought between the active site of FTase and that of GGTase I.

CONCLUSIONS

The compounds of the invention are true non-peptide Ras CAAX mimetics which have no amide bonds and lack any peptidic features of the tripeptide AAX. These mimetics are potent inhibitors of FTase and are highly selective for FTase over GGTase I. The structure-activity relationships demonstrate that a key feature for FTase recognition is the separation of a (R)-1,2-diamino-3-mercaptopropyl group and a carboxylic acid by a hydrophobic scaffold. The rigidity of this scaffold provides important information about the active site of FTase. These Ras CAAX mimetics have several desirable features in terms of drug design—small molecular weights, lack of peptidic features, high potency and specificity and resistance to metabolic inactivation.

In summary, the foregoing results show that the present compounds, which are characterized by their freedom from hydrolyzable groups and other peptidic features, demonstrate effective FTase inhibition while offering other advantages such as selective inhibition of farnesylation relative to geranylgeranylation, both in vitro and in vivo and freedom from metabolic inactivation by FTase.

REFERENCES

Literature references mentioned above are more specifically identified as follows, and are hereby incorporated by reference:

1. Barbacid, M., *Annu. Rev. Biochem.*, 56:779–929 (1987)
2. McCormick, F., *Nature*, 363:15–16 (1993)
3. Willumsen et al, *Nature*, 310:583–588 (1984)
4. Willumsen et al, *EMBO J.*, 3:2581–2585 (1984)
5. Hancock et al, *Cell*, 57:1167–1177 (1989)
6. Gutierrez et al, *EMBO J.*, 8:1093–1098 (1989)
7. Casey et al, *Proc. Natl. Acad. Sci. U.S.A.*, 86:8323–8327 (1989)
8. Jackson et al, *Proc. Natl. Acad. Sci. U.S.A.*, 87:3042–3046 (1990)
9. Hancock et al, *Cell*, 63:133–139 (1990)
10. Kato et al, *Proc. Natl. Acad. Sci. U.S.A.*, 89:6403–6407 (1992)
11. Gibbs, J. B., *Cell*, 65:1–4 (1991)
12. Gibbs et al, *Cell*, 77:175–178 (1994)
13. Reiss et al, *Cell*, 63:81–88 (1990)
14. Reiss et al, *J. Biol. Chem.*, 266:10672–10877 (1991)
15. Casey, P., *J. Lipid. Res.*, 88:1731–1740 (1992)
16. Cox et al, *Curr. Op. Cell Biol.*, 4:1008–1016 (1992)
17. Reiss et al, *Proc. Natl. Acad. Sci. U.S.A.*, 88:732–736 (1991)
18. Manne et al, *Proc. Natl. Acad. Sci. U.S.A.*, 87:7541–7545 (1990)
19. Moores et al, *J. Biol. Chem.*, 266:14603–14610 (1991)
20. Goldstein et al, *J. Biol. Chem.*, 266:15575–15578 (1991)
21. Brown et al, *Proc. Natl. Acad. Sci. U.S.A.*, 89:8313–8316 (1992)
22. Pompliano et al, *Biochemistry*, 31:3800–3807 (1992)
23. Kohl et al, *Science*, 260:1934–1937 (1993)
24. Graham et al, *J. Med. Chem.*, 37:725–732 (1994)
25. Garcia et al, *J. Biol. Chem.*, 268:18415–18418 (1993)
26. Nigam et al, *J. Biol. Chem.*, 268:20695–20698 (1993)
27. Qian et al, *J. Biol. Chem.*, 269:12410–12413 (1994)
28. Qian et al, *Bioorg. Med. Chem. Lett.*, 4:2579–2584, (1994)
29. Goldstein et al, *Science*, 260:1937–1942 (1993)
30. Watanabe et al, *Syn. Lett.*, 3:207–210 (1992)
31. Lacal et al, *Proc. Natl. Acad. Sci. U.S.A.*, 81:5305–5309 (19840
32. Cox et al, *Mol. Cell. Biol.*, 12:2606–2615 (1992)
33. Stradley et al, *Biochemistry*, 32:12586–12590 (1993)
34. Gardino, J. et al, *J. Org. Chem.*, 49: 5237–5243 (1984)
35. Wallow, T. I. et al. *J. Org. Chem.*: 59, 5034–5037 (1994)
36. Crowther, G. P. et al., *Org. Syn.*, 51: 96–100 (1971)
37. Fincham, C. I. et al., *J. Med. Chem.*, 35: 1472–1484 (1992)
38. Goel, O. P. et al., *Org. Syn.*, 67: 69–75 (1989)
39. Pearson, D. A. et al., *Tetrahedron Lett.*, 30: 2739–2742 (1989)
40. Vogt, A. et al., *J. Biol. Chem.*, 270: 660–664 (1995)

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
       (A) LENGTH: 4 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:1:

Cys Val Ile Met
   1

(2) INFORMATION FOR SEQ ID NO:2:

(i) SEQUENCE CHARACTERISTICS:
       (A) LENGTH: 4 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:2:

Cys Val Leu Ser

It will be appreciated that various modifications may be made in the invention as described above without departing from the scope and intent thereof as defined in the following claims wherein:

We claim:

1. A compound of the formula $$C^0 B$$

wherein $C^0$ stands for

A representing O or 2H, and $R_0$ representing SH, $NH_2$, or $C_xH_y$—$SO_2$—NH—, wherein $C_xH_y$ is a straight chain saturated or unsaturated hydrocarbon, with x being between 1 and 20 and y between 3 and 41, inclusive; and B stands for —NHR, where R is a biphenyl group optionally substituted with at least one moiety selected from carboxy, carbomethoxy, oxyalkyl, lower alkyl, aryl and tetrazoyl.

2. A compound according to claim 1 wherein $C^0$ is 3-mercapto-2-amino-propylamino.

3. A compound according to claim 2 wherein R is a biphenyl group substituted with —COOH.

4. A compound according to claim 2 wherein R is a biphenyl group substituted with lower alkyl or oxyalkyl.

5. A compound according to claim 4 wherein the lower alkyl is methyl.

6. A compound according to claim 1 of the formula:

wherein A is O or 2H; $R_1$ is hydrogen or COOH; $R_2$ is hydrogen, COOH, $COOCH_3$, $CH_3$ or tetrazolyl; $R_3$ is hydrogen or COOH; and $R_4$ is hydrogen, $OCH_3$, $OC_3H_7$ or a phenyl group.

7. A compound according to claim 6 wherein $R_1$ is hydrogen; $R_2$ is hydrogen, COOH or $CH_3$; $R_3$ is hydrogen or COOH, $R_2$ being COOH or $CH_3$ when $R_3$ is hydrogen; and $R_4$ is hydrogen.

8. A compound according to claim 7 wherein $R_2$ is COOH and $R_3$ is hydrogen.

9. A compound according to claim 6 wherein $R_1$ and $R_3$ are H, $R_2$ is COOH or $CH_3$, and $R_4$ is a phenyl or n-oxypropyl group.

10. A compound according to claim 6 wherein $R_1$, $R_3$, and $R_4$ are H; and $R_2$ is tetrazolyl.

11. A compound according to claim 1, wherein $R_0$ is $C_xH_y$—$SO_2$—NH—, x is 2–16 and y is 3 to 33.

12. A compound according to claim 11, wherein $R_0$ is selected from the group consisting of $C_2H_5$—$SO_2$—NH—, $CH_2$=CH—$SO_2$—NH—, and $CH_3(CH_2)_{15}$—$SO_2$—NH—.

13. A compound according to claim 1, wherein $R_0$ is $NH_2$—.

14. A compound according to claim 13, wherein R is a 3'-carboxy-biphenyl group or 2-methoxy-3'-carboxy-biphenyl group.

15. A compound according to claim 1 wherein $R_0$ is SH and B is 3-aminomethyl-3'-carboxybiphenyl.

16. A pharmaceutical composition comprising a compound according to claim 2 and a pharmaceutically acceptable carrier therefor.

17. A pharmaceutical composition comprising a compound according to claim 1 and a pharmaceutically acceptable carrier therefor.

18. A method of inhibiting p21ras farnesyltransferase in a host in need of such inhibition which comprises administering to said host an effective amount of a compound according to claim 2.

19. A compound of the formula $$C^1B$$

wherein
$C^1$ stands for $R_0$ representing SH, $NH_2$, or $C_xH_y$—$SO_2$—NH—, wherein $C_xH_y$ is a straight chain saturated or unsaturated hydrocarbon, with x being between 1 and 20 and y between 3 and 41, inclusive; and B stands for —NHR, where R is an aryl group optionally substituted with at least one moiety selected from carboxy, carbomethoxy, oxyalkyl, lower alkyl, aryl and tetrazoyl.

20. A pharmaceutical composition comprising a compound according to claim 19 and a pharmaceutically acceptable carrier therefor.

21. A method of inhibiting p21ras farnesyltransferase in a host in need of such inhibition which comprises administering to said host an effective amount of a compound of formula $$C^0B$$

wherein $C^0$ stands for

A representing O or 2H, and $R_0$ representing SH, $NH_2$, or $C_xH_y$—$SO_2$—NH—, wherein $C_xH_y$ is a straight chain saturated or unsaturated hydrocarbon, with x being between 1 and 20 and y between 3 and 41, inclusive; and B stands for —NHR, where R is an aryl group optionally substituted with at least one moiety selected from carboxy, carbomethoxy, oxyalkyl, lower alkyl, aryl and tetrazoyl.

* * * * *